(12) United States Patent
Schwarz et al.

(10) Patent No.: US 8,629,273 B2
(45) Date of Patent: *Jan. 14, 2014

(54) DIAZINYLPYRAZOLYL COMPOUNDS

(75) Inventors: Hans-Georg Schwarz, Dorsten (DE); Robert Velten, Langenfeld (DE); Achim Hense, Leverkusen (DE); Simon Maechling, Tokyo (JP); Stefan Werner, Monheim (DE); Bernd Alig, Königswinter (DE); Eva-Maria Franken, Leichlingen (DE); Arnd Voerste, Köln (DE); Ulrich Görgens, Ratingen (DE)

(73) Assignee: Bayer Intellectual Property GmbH, Monheim (DE)

( * ) Notice: Subject to any disclaimer, the term of this patent is extended or adjusted under 35 U.S.C. 154(b) by 144 days.

This patent is subject to a terminal disclaimer.

(21) Appl. No.: 12/944,482

(22) Filed: Nov. 11, 2010

(65) Prior Publication Data

US 2011/0124660 A1 May 26, 2011

Related U.S. Application Data

(60) Provisional application No. 61/260,107, filed on Nov. 11, 2009.

(30) Foreign Application Priority Data

Nov. 11, 2009 (EP) .................................. 09175661

(51) Int. Cl.
| | |
|---|---|
| C07D 403/04 | (2006.01) |
| A61K 31/4155 | (2006.01) |
| A61K 31/501 | (2006.01) |
| A01N 43/56 | (2006.01) |
| A01N 43/60 | (2006.01) |

(52) U.S. Cl.
USPC ...................... 544/406; 514/252.1

(58) Field of Classification Search
USPC ...................... 544/406; 514/252.1
See application file for complete search history.

(56) References Cited

U.S. PATENT DOCUMENTS

| | | | |
|---|---|---|---|
| 5,849,778 A | 12/1998 | Heil et al. | |
| 6,169,086 B1 | 1/2001 | Ejima et al. | |
| 7,087,616 B2 | 8/2006 | Fischer et al. | |
| 7,514,464 B2 | 4/2009 | Billen et al. | |
| 2006/0014802 A1 | 1/2006 | Billen et al. | |
| 2010/0144672 A1 | 6/2010 | Frackenpohl et al. | |
| 2011/0021539 A1* | 1/2011 | Schwarz et al. | 514/255.05 |

FOREIGN PATENT DOCUMENTS

| | | |
|---|---|---|
| WO | WO 95/22530 A1 | 8/1995 |
| WO | WO 98/32739 A1 | 7/1998 |
| WO | WO 02/068413 A1 | 9/2002 |
| WO | WO 2006/032462 A1 | 3/2006 |
| WO | WO 2007/027842 A1 | 3/2007 |
| WO | WO 2007/048733 A1 | 5/2007 |
| WO | WO 2007/048734 A1 | 5/2007 |
| WO | WO 2007/149134 A1 | 12/2007 |
| WO | WO 2008/077483 A1 | 7/2008 |
| WO | WO 2008/104503 A1 | 9/2008 |
| WO | WO 2010/136145 A1 | 12/2010 |

OTHER PUBLICATIONS

Baraldi, P.G., et al., "Synthesis of new pyrazolo[4,3-e]1,2,4-triazolo[1,5-c]pyrimidine and 1,2,3-trialzolo[4,3-e]1,2,4-triazolo[1,5-c] pyrimidine displaying potent and selective activity as $A_{2a}$ adenosine receptor antagonists,"*Bioorg. Med. Chem. Lett.* 4(21):2539-2544, Elsevier Science Ltd., England (1994).
Chesterfield, J. et al., "Pyrimidines. Part VIII. Halogeno- and Hidrazino-pyrimidines," *J. Chem. Soc.*:3478-3481, Chemical Society, England (1955).
Ducray, R., et al., "Novel 3-alkoxy-1H-pyrazolo[3,4-d]pyrimodines as EGFR and erbB2 receptor tyrosine kinase inhibitors," *Bioorg. Med. Chem. Lett.* 18: 959-962, Elsevier Ltd., England (2008).
Gatta, F., et al., "Synthesis imidazo[1,2-c]pyrazolo[4,3-e]pyrimidine, pyrazolo[4,3-e]1,2,4-trialzolo[1,5-c]pyrimidine and 1,2,4-trialzolo[1,5-i]purines: new potent adenosine $A_2$ receptor antagonists," *Eur. J. Med. Chem. Lett.* 28:569-576, Elsevier France (1993).
Hosmane, R.S. and Lim, B.B., "A Novel Method for the Sysnthesis of 9-Benzyl-6-(2-methyl-hydrazino)purine and 1-Mehtyl-4-(2-methylhydrazino)-1H-pyrazolo[3,4-d]pyrimidine," Synthesis 3:242-244, Thieme, Germany (1998).
Hosmane, R.S., et al., "Rearrangements in Heterocyclic Synthesis: A Novel Translocation of an (N-amino-N-methylamino)methylene Group from a Heterocyclic N-amino-N-methylformamindine Side Chain to the Vinylogous Nitrile Function," *J. Org. Chem.* 53:382-386, American Chemical Society, United States (1988).
Nes, W.R. and Burger, A., "Amine and Enol Derivatives of 1,1,1-Trifluoropropane," *J. Am. Chem. Soc.* 72: 5409-5413, American Chemical Society, United States (1950).
International Search Report for International Appl. No. PCT/EP2009/003072, European Patent Office, Rijswijk, Netherlands, mailed Jul. 28, 2009.
Schallner, O., "Hetaryl-hydrazine" in *Methoden der Organischen Chemie (Houben-Weyl)*, vol. XI, Part I, pp. 678-798 (Eugen Müllen ed., Georg Thieme Verlag, Stuttgart, 1957).

* cited by examiner

*Primary Examiner* — Venkataraman Balasubramanian
(74) *Attorney, Agent, or Firm* — Sterne, Kessler, Goldstein & Fox P.L.L.C.

(57) ABSTRACT

The present invention relates to diazinylpyrazolyl compounds of the formula (I)

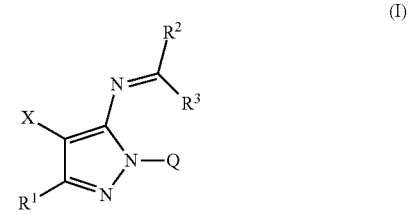

where $R^1$ to $R^3$, X and Q are as defined in the description, and to their use in crop protection, in particular as insecticides, and also to processes for their preparation and compositions comprising such diazinylpyrazolylimines and -imidoates.

6 Claims, No Drawings

DIAZINYLPYRAZOLYL COMPOUNDS

The present invention relates to diazinylpyrazolyl compounds, in particular diazinylpyrazolylimines and diazinylpyrazolylimidoates, and to their use in crop protection, in particular as insecticides, and also to processes for their preparation and to compositions comprising such diazinylpyrazolylimines and -imidoates.

It is known that certain pyrimidinylpyrazoles can be used as intermediates in the synthesis of N-pyrazolylanilines and N-pyrazolylaminopyridines (WO 1995/22530).

Furthermore, WO 2007/027842 proposes the use of certain pyrazole compounds, in particular anilinopyrazoles substituted in the 1-position of the pyrazole group by 2-pyrazines, for the treatment of diabetes.

The use of certain pyrimidinylpyrazoles in crop protection is likewise already known. Thus, for example, WO 2002/68413 proposes the use of pyrimidinylpyrazoles containing a 4-pyrimidinyl radical for controlling insects. WO 2007/048733 and WO 2007/048734 disclose the use of certain aminopyrazoles for controlling phytopathogenic fungi.

A more recent publication (WO 2008/077483) describes further pyrimidinylpyrazoles which are used as insecticides and which can be described by the general formula below

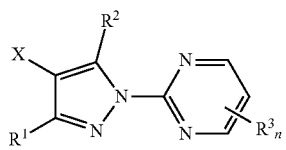

in which $R^2$ represents alkylamino or benzylamino, inter alia.

Since the ecological and economical demands made on modern crop protection agents are increasing constantly, for example with respect to toxicity, selectivity, application rate, formation of residues and favourable manufacture, and there can furthermore be problems, for example, with resistances, there is a constant need to develop novel crop protection agents which, at least in some areas, have advantages over the known agents.

Accordingly, it is an object of the present invention to provide further insecticides from the group of the pyrimidinylpyrazoles which, compared to known active compounds, have improved activity and/or a broader activity spectrum and avoid the disadvantages mentioned above.

We have now found novel diazinylpyrazolylimines and -imidoates which avoid the disadvantages mentioned above and have a high efficacy.

Accordingly, the invention relates to the novel diazinylpyrazolyl compounds and their salts and N-oxides of the formula (I)

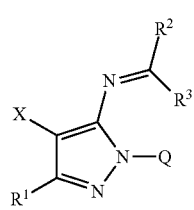

in which
X represents substituted aryl or heteroaryl, preferably phenyl, 2-pyridyl or 3-pyridyl, each of which is at least monosubstituted by a substituent Y, where
Y represents halogen, cyano, nitro, $C_1$-$C_6$-alkyl, halo-$C_1$-$C_6$-alkyl, $C_1$-$C_6$-alkoxy, $C_1$-$C_6$-alkoxy-$C_1$-$C_6$-alkyl, $C_1$-$C_6$-alkoxy-$C_1$-$C_6$-alkoxy, $C_3$-$C_6$-cycloalkyl, $C_2$-$C_6$-alkenyloxy, $C_2$-$C_6$-alkynyloxy, benzyloxy, $C_3$-$C_6$-cycloalkyl-$C_1$-$C_6$-alkoxy, halo-$C_1$-$C_6$-alkoxy, halo-$C_1$-$C_6$-alkoxy-$C_1$-$C_6$-alkyl, $C_1$-$C_6$-alkylsulphanyl, halo-$C_1$-$C_6$-alkylsulphanyl, $C_1$-$C_6$-alkylsulphinyl, halo-$C_1$-$C_6$-alkylsulphinyl, $C_1$-$C_6$-alkylsulphonyl, halo-$C_1$-$C_6$-alkylsulphonyl, $C_1$-$C_6$-alkylcarbonyl, $C_1$-$C_6$-alkoxycarbonyl, $C_1$-$C_6$-alkoxycarbonyl-$C_1$-$C_6$-alkyl, carboxyl, carboxamide, di-$C_1$-$C_6$-alkylcarboxamide, tri-$C_1$-$C_6$-alkylsilyl, amino, $C_1$-$C_6$-alkylamino, di-$C_1$-$C_6$-alkylamino, $C_1$-$C_6$-alkylsulphonylamino, di-$C_1$-$C_6$-alkylsulphonylamino, formyl, —CH=NO—H, —CH=NO-halo-$C_1$-$C_6$-alkyl, —C(CH$_3$)=NO—H, —C(CH$_3$)=NO—$C_1$-$C_6$-alkyl or —C(CH$_3$)=NO-halo-$C_1$-$C_6$-alkyl, where, if two substituents Y are present and these represent two vicinal $C_1$-$C_6$-alkyl-, halo-$C_1$-$C_6$-alkyl-, $C_1$-$C_6$-alkoxy- and/or halo-$C_1$-$C_6$-alkoxy groups, the substituents together with the carbon atoms to which they are attached form a five- or six-membered cyclic system which contains 0 to 2 oxygen or nitrogen atoms, where the carbon atoms of the cyclic system may be substituted by one or more halogen atoms and/or $C_1$-$C_6$-alkyl radicals; Y preferably represents halogen, halo-$C_1$-$C_6$-alkyl, $C_1$-$C_6$-alkyl, $C_1$-$C_6$-alkoxy, particularly preferably F, Cl, Br, I, CF$_3$, methyl, ethyl, isopropyl, n-propyl, n-butyl, isobutyl, s-butyl, t-butyl, methoxy, ethoxy, n-propoxy or isopropoxy;
$R^1$ represents $C_1$-$C_6$-alkyl oder substituted $C_1$-$C_6$-alkyl which is substituted by one or more substituents selected from the group consisting of $C_1$-$C_6$-alkoxy, halo-$C_1$-$C_6$-alkoxy, $C_1$-$C_6$-alkylsulphanyl, halo-$C_1$-$C_6$-alkylsulphanyl, $C_1$-$C_6$-alkylsulphinyl, halo-$C_1$-$C_6$-alkylsulphinyl, $C_1$-$C_6$-alkylsulphonyl, halo-$C_1$-$C_6$-alkylsulphonyl, $C_1$-$C_6$-alkylcarbonyl, $C_1$-$C_6$-alkoxycarbonyl, hydroxyl and $C_3$-$C_6$-cycloalkyl, represents $C_2$-$C_6$-alkenyl or substituted $C_2$-$C_6$-alkenyl which is substituted by one or more substituents selected from the group consisting of halogen, $C_1$-$C_6$-alkoxy, halo-$C_1$-$C_6$-alkoxy, $C_1$-$C_6$-alkylsulphanyl, halo-$C_1$-$C_6$-alkylsulphanyl, $C_1$-$C_6$-alkylsulphinyl, halo-$C_1$-$C_6$-alkylsulphinyl, $C_1$-$C_6$-alkylsulphonyl, halo-$C_1$-$C_6$-alkylsulphonyl, $C_1$-$C_6$-alkylcarbonyl, $C_1$-$C_6$-alkoxycarbonyl and $C_3$-$C_6$-cycloalkyl, represents $C_3$-$C_6$-cycloalkyl or substituted $C_3$-$C_6$-cycloalkyl which is substituted by one or more substituents selected from the group consisting of $C_1$-$C_6$-alkyl, halo-$C_1$-$C_6$-alkyl and halogen, represents halo-$C_1$-$C_6$-alkyl or substituted halo-$C_1$-$C_6$-alkyl which is substituted by one or more substituents selected from the group consisting of $C_1$-$C_6$-alkoxy, $C_1$-$C_6$-alkylsulphanyl, halo-$C_1$-$C_6$-alkylsulphanyl, $C_1$-$C_6$-alkylsulphinyl, halo-$C_1$-$C_6$-alkylsulphinyl, $C_1$-$C_6$-alkylsulphonyl, halo-$C_1$-$C_6$-alkylsulphonyl and phenyl, optionally monosubstituted or independently of one another polysubstituted by halogen, $C_1$-$C_6$-alkyl, halo-$C_1$-$C_6$-alkyl and $C_1$-$C_6$-alkoxy, represents phenyl or substituted phenyl which is substituted by one or more substituents selected from the group consisting of halogen, $C_1$-$C_6$-alkyl, halo-$C_1$-$C_6$-alkyl and $C_1$-$C_6$-alkoxy, represents benzyl or substituted benzyl which is substituted by one or more substituents selected from the group consisting of halogen, $C_1$-$C_6$-alkyl, halo-$C_1$-$C_6$-alkyl and $C_1$-$C_6$-alkoxy, or represents cyano, formyl, $C_1$-$C_6$-alkylcarbonyl, —CH=NO—H, —CH=NO—$C_1$-$C_6$-alkyl, —CH=NO-halo-$C_1$-$C_6$-alkyl, —C($CH_3$)=NO—H, —C($CH_3$)=NO—$C_1$-$C_6$-alkyl or —C($CH_3$)=NO-halo-$C_1$-$C_6$-alkyl; $R^1$ preferably represents halo-$C_1$-$C_6$-alkyl, $C_1$-$C_6$-alkyl or $C_3$-$C_6$-cycloalkyl, particularly preferably $CF_3$, $C_2F_5$, $CF_2Cl$, $CF_2Br$, n-$C_3F_7$, i-$C_3F_7$, CH(F)$CH_3$, methyl, ethyl, isopropyl, n-propyl, n-butyl, isobutyl, s-butyl, t-butyl or cyclopropyl;

$R^2$ represents hydrogen or represents $C_1$-$C_6$-alkyl or substituted $C_1$-$C_6$-alkyl which is substituted by one or more substituents selected from the group consisting of $C_1$-$C_6$-alkoxy, halo-$C_1$-$C_6$-alkoxy, $C_1$-$C_6$-alkylsulphanyl, halo-$C_1$-$C_6$-alkylsulphanyl, $C_1$-$C_6$-alkylsulphinyl, halo-$C_1$-$C_6$-alkylsulphinyl, $C_1$-$C_6$-alkylsulphonyl, halo-$C_1$-$C_6$-alkylsulphonyl, $C_1$-$C_6$-alkylcarbonyl, $C_1$-$C_6$-alkoxycarbonyl, hydroxyl and $C_3$-$C_6$-cycloalkyl, represents $C_2$-$C_6$-alkenyl or substituted $C_2$-$C_6$-alkenyl which is substituted by one or more substituents selected from the group consisting of halogen, $C_1$-$C_6$-alkoxy, halo-$C_1$-$C_6$-alkoxy, $C_1$-$C_6$-alkylsulphanyl, halo-$C_1$-$C_6$-alkylsulphanyl, $C_1$-$C_6$-alkylsulphinyl, halo-$C_1$-$C_6$-alkylsulphinyl, $C_1$-$C_6$-alkylsulphonyl, halo-$C_1$-$C_6$-alkylsulphonyl, $C_1$-$C_6$-alkylcarbonyl, $C_1$-$C_6$-alkoxycarbonyl and $C_3$-$C_6$-cycloalkyl, represents $C_3$-$C_6$-cycloalkyl or substituted $C_3$-$C_6$-cycloalkyl which is substituted by one or more substituents selected from the group consisting of $C_1$-$C_6$-alkyl, halo-$C_1$-$C_6$-alkyl and halogen, represents halo-$C_1$-$C_6$-alkyl or substituted halo-$C_1$-$C_6$-alkyl which is substituted by one or more substituents selected from the group consisting of $C_1$-$C_6$-alkoxy, $C_1$-$C_6$-alkylsulphanyl, halo-$C_1$-$C_6$-alkylsulphanyl, $C_1$-$C_6$-alkylsulphinyl, halo-$C_1$-$C_6$-alkylsulphinyl, $C_1$-$C_6$-alkylsulphonyl, halo-$C_1$-$C_6$-alkylsulphonyl and phenyl, optionally monosubstituted or independently of one another polysubstituted by halogen, $C_1$-$C_6$-alkyl, halo-$C_1$-$C_6$-alkyl and/or $C_1$-$C_6$-alkoxy, represents phenyl or substituted phenyl which is substituted by one or more substituents selected from the group consisting of halogen, $C_1$-$C_6$-alkyl, halo-$C_1$-$C_6$-alkyl, hydroxyl and $C_1$-$C_6$-alkoxy, represents heteroaryl or substituted heteroaryl which is substituted by one or more substituents selected from the group consisting of —OH, —SH, —$NH_2$, halogen, $C_1$-$C_6$-alkyl, halo-$C_1$-$C_6$-alkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro and cyano, represents heterocyclyl or substituted heterocyclyl which is substituted by one or more substituents selected from the group consisting of —OH, =O, —SH, =S, —$NH_2$, halogen, $C_1$-$C_6$-alkyl, halo-$C_1$-$C_6$-alkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro and cyano, represents benzyl or substituted benzyl which is substituted by one or more of the substituents selected from the group consisting of halogen, $C_1$-$C_6$-alkyl, halo-$C_1$-$C_6$-alkyl and $C_1$-$C_6$-alkoxy, represents heteroaryl-$C_1$-$C_3$-alkyl or substituted heteroaryl-$C_1$-$C_3$-alkyl which is substituted by one or more of the substituents selected from the group consisting of —OH, —SH, —$NH_2$, halogen, $C_1$-$C_6$-alkyl, halo-$C_1$-$C_6$-alkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro and cyano, represents heterocyclyl-$C_1$-$C_3$-alkyl or substituted heteroaryl-$C_1$-$C_3$-alkyl which is substituted by one or more substituents selected from the group consisting of —OH, =O, —SH, =S, —$NH_2$, halogen, $C_1$-$C_6$-alkyl, halo-$C_1$-$C_6$-alkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro and cyano, or represents chlorine, cyano, formyl, $C_1$-$C_6$-alkylcarbonyl, —CH=NO—H, —CH=NO—$C_1$-$C_6$-alkyl, —CH=NO-halo-$C_1$-$C_6$-alkyl, —C($CH_3$)=NO—H, —C($CH_3$)=NO—$C_1$-$C_6$-alkyl or —C($CH_3$)=NO-halo-$C_1$-$C_6$-alkyl; $R^2$ preferably represents hydrogen or $C_1$-$C_6$-alkyl and particularly preferably hydrogen or methyl;

$R^3$ represents $C_1$-$C_6$-alkyl or represents substituted $C_1$-$C_6$-alkyl which is substituted by one or more substituents selected from the group consisting of $C_1$-$C_6$-alkoxy, halo-$C_1$-$C_6$-alkoxy, $C_1$-$C_6$-alkylsulphanyl, halo-$C_1$-$C_6$-alkylsulphanyl, $C_1$-$C_6$-alkylsulphinyl, halo-$C_1$-$C_6$-alkylsulphinyl, $C_1$-$C_6$-alkylsulphonyl, halo-$C_1$-$C_6$-alkylsulphonyl, $C_1$-$C_6$-alkylcarbonyl, $C_1$-$C_6$-alkoxycarbonyl, hydroxyl and $C_3$-$C_6$-cycloalkyl, represents $C_2$-$C_6$-alkenyl or substituted $C_2$-$C_6$-alkenyl substituted by one or more substituents selected from the group consisting of halogen, $C_1$-$C_6$-alkoxy, halo-$C_1$-$C_6$-alkoxy, $C_1$-$C_6$-alkylsulphanyl, halo-$C_1$-$C_6$-alkylsulphanyl, $C_1$-$C_6$-alkylsulphinyl, halo-$C_1$-$C_6$-alkylsulphinyl, $C_1$-$C_6$-alkylsulphonyl, halo-$C_1$-$C_6$-alkylsulphonyl, $C_1$-$C_6$-alkylcarbonyl, $C_1$-$C_6$-alkoxycarbonyl and $C_3$-$C_6$-cycloalkyl, represents $C_3$-$C_6$-cycloalkyl or substituted $C_3$-$C_6$-cycloalkyl which is substituted by one or more substituents selected from the group consisting of $C_1$-$C_6$-alkyl, halo-$C_1$-$C_6$-alkyl and halogen, represents halo-$C_1$-$C_6$-alkyl or substituted halo-$C_1$-$C_6$-alkyl which is substituted by one or more substituents selected from the group consisting of $C_1$-$C_6$-alkoxy, $C_1$-$C_6$-alkylsulphanyl, halo-$C_1$-$C_6$-alkylsulphanyl, $C_1$-$C_6$-alkylsulphinyl, halo-$C_1$-$C_6$-alkylsulphinyl, $C_1$-$C_6$-alkylsulphonyl, halo-$C_1$-$C_6$-alkylsulphonyl and phenyl, optionally monosubstituted or independently of one another polysubstituted by halogen, $C_1$-$C_6$-alkyl, halo-$C_1$-$C_6$-alkyl and $C_1$-$C_6$-alkoxy, represents phenyl or substituted phenyl which is substituted by one or more substituents selected from the group consisting of halogen, $C_1$-$C_6$-alkyl, halo-$C_1$-$C_6$-alkyl, hydroxyl and $C_1$-$C_6$-alkoxy, represents heteroaryl or substituted heteroaryl which is substituted by one or more substituents selected from the group consisting of —OH, —SH, —$NH_2$, halogen, $C_1$-$C_6$-alkyl, halo-$C_1$-$C_6$-alkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro and cyano, represents heterocyclyl or substituted heterocyclyl which is substituted by one or more substituents selected from the group consisting of —OH, =O, —SH, =S, —$NH_2$, halogen, $C_1$-$C_6$-alkyl, halo-$C_1$-$C_6$-alkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro and cyano, represents benzyl or substituted benzyl which is substituted by one or more substituents selected from the group consisting of halogen, $C_1$-$C_6$-alkyl, halo-$C_1$-$C_6$-alkyl and $C_1$-$C_6$-alkoxy, represents heteroaryl-$C_1$-$C_3$-alkyl or substituted heteroaryl-$C_1$-$C_3$-alkyl which is substituted by one or more substituents selected from the group consisting of —OH, —SH, —$NH_2$, halogen, $C_1$-$C_6$-alkyl, halo-$C_1$-$C_6$-alkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro and cyano, represents heterocyclyl-$C_1$-$C_3$-alkyl or substituted heterocyclyl-$C_1$-$C_3$-alkyl which is substituted by one or more substituents selected from the group consisting of OH, =O, SH, =S, $NH_2$, halogen, $C_1$-$C_6$-alkyl, halo-$C_1$-$C_6$-alkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro and cyano, or represents chlorine, cyano, formyl, $C_1$-$C_6$-alkylcarbonyl, —CH=NO—H, —CH=NO—$C_1$-$C_6$-alkyl, —CH=NO-halo-$C_1$-$C_6$-alkyl, —C($CH_3$)=NO—H, —C($CH_3$)=NO—$C_1$-$C_6$-alkyl or —C($CH_3$)=NO-halo-$C_1$-$C_6$-alkyl, $C_1$-$C_6$-alkoxy, $C_3$-$C_6$-cycloalkoxy, $C_3$-$C_6$-cycloalkyl-$C_1$-$C_6$-alkoxy, halo-$C_1$-$C_6$-alkoxy, $C_2$-$C_6$-alkenyloxy, $C_2$-$C_6$-alkynyloxy, represents benzyloxy or substituted benzyloxy which is substituted by one or more substituents selected from the group consisting of halogen, $C_1$-$C_6$-alkyl, halo-$C_1$-$C_6$-alkyl and $C_1$-$C_6$-alkoxy, represents $C_1$-$C_6$-alkylsulphanyl, $C_1$-$C_6$-alkylsulphinyl, $C_1$-$C_6$-alkylsulphonyl, represents phenylsulphanyl, phenylsulphinyl or phenylsulphonyl or phenylsulphanyl, phenylsulphinyl or phenylsulphonyl, each of which is substituted at the phenyl group by one or more substituents selected from the group consisting of halogen, $C_1$-$C_6$-alkyl, halo-$C_1$-$C_6$-alkyl and $C_1$-$C_6$-alkoxy, represents substituted amino which is mono- or disubstituted by one or more substituents selected from the group consisting of $C_1$-$C_6$-alkyl, halo-$C_1$-$C_6$-alkyl, $C_2$-$C_6$-alkenyl, $C_2$-$C_6$-alkynyl, benzyl which is optionally monosubstituted or independently of one another polysubstituted by halogen, $C_1$-$C_6$-alkyl, $C_1$-$C_6$-haloalkyl and/or $C_1$-$C_6$-alkoxy, phenyl or substituted phenyl which is substituted by one or more substituents selected from the group consisting of OH, halogen, $C_1$-$C_6$-alkyl, halo-$C_1$-$C_6$-alkyl and $C_1$-$C_6$-alkoxy, represents amino as component of a five- or six-membered heterocyclic ring which is attached via the amino nitrogen and, as additional heteroatom, may contain oxygen and/or nitrogen; $R^3$ preferably represents phenyl or phenyl which is substituted by one or more substituents selected from the group consisting of OH, halogen, $C_1$-$C_6$-alkyl, halo-$C_1$-$C_6$-alkyl and $C_1$-$C_6$-alkoxy, $C_1$-$C_6$-alkoxy and substituted amino which his disubstituted by $C_1$-$C_6$-alkyl and particularly preferably represents phenyl or phenyl which is substituted by one or more substituents selected from the group consisting of OH, F, Cl, Br, $CF_3$, methyl and methoxy, represents methoxy, ethoxy, n-propoxy, isopropoxy, n-butoxy, N,N-dimethylamino or N-ethyl-N-methylamino;

Q represents a chemical grouping $Q^1$ or $Q^2$

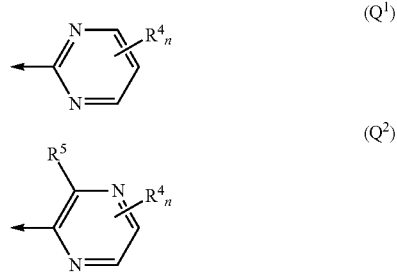

in which $R^4$ represents halogen, $C_1$-$C_6$-alkyl, $C_3$-$C_6$-cycloalkyl, halo-$C_1$-$C_6$-alkyl, cyano, formyl, $C_1$-$C_6$-alkylcarbonyl, —CH=NO—H, —CH=NO—$C_1$-$C_6$-alkyl, —CH=NO-halo-$C_1$-$C_6$-alkyl, —C($CH_3$)=NO—H, —C($CH_3$)=NO—$C_1$-$C_6$-alkyl, —C($CH_3$)=NO-halo-$C_1$-$C_6$-alkyl, nitro, amino, hydroxyl, SH, $C_1$-$C_6$-alkoxy, $C_1$-$C_6$-alkylsulphanyl, halo-$C_1$-$C_6$-alkylsulphanyl, $C_1$-$C_6$-alkylsulphinyl, halo-$C_1$-$C_6$-alkylsulphinyl, $C_1$-$C_6$-alkylsulphonyl or halo-$C_1$-$C_6$-alkylsulphonyl; $R^4$ preferably represents nitro, halogen, $C_1$-$C_6$-alkyl, amino and particularly preferably represents F and Cl;

n represents 0, 1, 2 or 3; preferably represents 0 or 1 and particularly preferably represents 0; and $R^5$ represents hydrogen, halogen, $C_1$-$C_6$-alkyl, halo-$C_1$-$C_6$-alkyl, hydroxyl, $C_1$-$C_6$-alkoxy, $C_1$-$C_6$-alkoxy-$C_1$-$C_6$-alkyl, $C_1$-$C_6$-alkoxy-$C_1$-$C_6$-alkoxy, $C_3$-$C_6$-cycloalkyl, $C_2$-$C_6$-alkenyloxy, $C_2$-$C_6$-alkynyloxy, benzyloxy, $C_3$-$C_6$-cycloalkyl-$C_1$-$C_6$-alkoxy, halo-$C_1$-$C_6$-alkoxy, halo-$C_1$-$C_6$-alkoxy-$C_1$-$C_6$-alkyl, —SH, $C_1$-$C_6$-alkylsulphanyl, halo-$C_1$-$C_6$-alkylsulphanyl, $C_1$-$C_6$-alkylsulphinyl, halo-$C_1$-$C_6$-alkylsulphinyl, $C_1$-$C_6$-alkylsulphonyl, halo-$C_1$-$C_6$-alkylsulphonyl, cyano, nitro, $C_1$-$C_6$-alkylcarbonyl, $C_1$-$C_6$-alkoxycarbonyl, $C_1$-$C_6$-alkoxycarbonyl-$C_1$-$C_6$-alkyl, carboxyl, carboxamide, di-$C_1$-$C_6$-alkylcarboxamide, tri-$C_1$-$C_6$-alkylsilyl, nitro, amino, $C_1$-$C_6$-alkylamino, di-$C_1$-$C_6$-alkylamino, $C_1$-$C_6$-alkylsulphonylamino, di-$C_1$-$C_6$-alkylsulphonylamino, formyl, —CH=NO—H, —CH=NO—$C_1$-$C_6$-alkyl, —CH=NO-halo-$C_1$-$C_6$-alkyl, —C($CH_3$)=NO—H, —C($CH_3$)=NO—$C_1$-$C_6$-alkyl, —C($CH_3$)=NO-halo-$C_1$-$C_6$-alkyl, or represents heteroaryl or substituted heteroaryl which is substituted by one or more substituents selected from the group consisting of halogen, $C_1$-$C_6$-alkyl, halo-$C_1$-$C_6$-alkyl and $C_1$-$C_6$-alkoxy; $R^5$ preferably represents halogen, $C_1$-$C_6$-alkoxy, $C_1$-$C_6$-haloalkyl and particularly preferably represents F, Cl, Br, I, methoxy, ethoxy, isopropoxy, n-propoxy and $CF_3$.

The compounds according to the invention have good insecticidal and parasiticidal properties and can be used in crop protection, in veterinary medicine and in the protection of materials for controlling unwanted pests, such as insects, spider mites, endo- or ectoparasites.

By addition of a suitable inorganic or organic acid (for example HCl, HBr, $H_2SO_4$ or $HNO_3$, oxalic acid or sulphonic acids) onto a basic group (for example amino or alkylamino), the compounds of the formula (I) may form acid addition salts. Substituents, such as, for example, sulphonic acids or carboxylic acids, which are present in deprotonated form, may form inner salts with groups which for their part can be protonated, such as amino groups. Salts may also be formed by replacing the hydrogen of suitable substituents, such as, for example, sulphonic acids or carboxylic acids, by an agriculturally suitable cation. These salts are, for example, metal salts, in particular alkali metal salts or alkaline earth metal salts, in particular sodium salts and potassium salts, or else ammonium salts, salts with organic amines or quartary ammonium salts having cations of the formula [NRR'R"R"']+ in which R to R'" each independently represent an organic radical, in particular alkyl, aryl, aralkyl or alkylaryl.

According to the invention, "alkyl" —on its own or as component of a chemical group—represents straight-chain or branched hydrocarbon radicals having preferably 1 to 6 carbon atoms, such as, for example, methyl, ethyl, propyl, such as n- or isopropyl, butyl, such as n-, iso-, t- or 2-butyl, pentyl, such as n-pentyl, isopentyl or neopentyl, hexyl, such as n-hexyl, isohexyl, 3-methylpentyl, 2,2-dimethylbutyl and 2,3-dimethylbutyl. More preference is given to alkyls having 1 to 4 carbon atoms, such as, inter alia, methyl, ethyl, n-propyl, isopropyl, n-butyl, isobutyl, sec-butyl or tert-butyl. The alkyls according to the invention may be substituted by one or more identical or different radicals.

According to the invention, "alkenyl" —on its own or as component of a chemical group—represents straight-chain or branched hydrocarbons having preferably 2 to 6 carbon atoms and at least one double bond, such as, for example, vinyl, 1-allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. More preference is given to alkenyls having 2 to 4 carbon atoms. The alkenyls according to the invention may be substituted by one or more identical or different radicals.

According to the invention, "alkynyl"—on its own or as part of a chemical group—represents straight-chain or branched hydrocarbons having preferably 2 to 6 carbon atoms and at least one triple bond, such as, for example, ethynyl, propargyl/propinyl, but-2-yn-1-yl, but-3-yn-1-yl and 1-methylbut-3-yn-1-yl. More preference is given to alkynyls having 2 to 4 carbon atoms. The alkynyls according to the invention may be substituted by one or more identical or different radicals.

According to the invention, "cycloalkyl"—on its own or as component of a chemical group—represents mono-, bi- or tricyclic hydrocarbons having preferably 3 to 6 carbon atoms, such as, for example, cyclopropyl, cyclobutyl, cyclopentyl or cyclohexyl. More preference is given to cycloalkyls having 3, 4 or 5 carbon atoms, such as, for example, cyclopropyl or cyclobutyl. The cycloalkyls according to the invention may be substituted with one or more identical or different radicals.

According to the invention, "halogen" represents fluorine, chlorine, bromine or iodine, in particular fluorine, chlorine or bromine.

The halogen-substituted chemical groups according to the invention, such as, for example, haloalkyl, halocycloalkyl, haloalkoxy, haloalkenyl, haloalkynyl are mono- or polysubstituted, up to the maximum possible number of substituents, by halogen. In the case of polysubstitution by halogen, the halogen atoms may be identical or different and may be attached to one or a plurality of carbon atoms. The term includes monohaloalkyls and perhaloalkyl. Here, halogen represents in particular fluorine, chlorine, bromine or iodine, preferably fluorine, chlorine or bromine and particularly preferably chlorine and/or fluorine.

Examples of haloalkyls and haloalkenyls, haloalkynyls and haloalkoxy, respectively, are trifluoromethyl, difluoromethyl, trichloromethyl, chlorodifluoromethyl, dichlorofluoromethyl, chloromethyl, bromomethyl, 1-fluoroethyl, 2-fluoroethyl, 2,2-difluoroethyl, 2,2,2-trifluoroethyl, 1,1-difluoroethyl, 1,1,2,2-tetrafluoroethyl, trifluoroallyl and 1-chloroprop-1-yl, 2,2,2-trichloroethyl, 2-chloro-2,2-difluoroethyl, pentafluoroethyl and pentafluoro-tert-butyl, or $CF_3$, $CHF_2$, $CH_2F$, $CF_3CF_2$, $CF_3CHF_2$, $CHFCH_3$, $CF_2CH_3$, $CH_2FCHCl$, $CCl_3$, $CHCl_2$, $CH_2CH_2Cl$, $OCF_3$, $OCHF_2$, $OCH_2F$, $CF_3CF_2O$, $OCH_2CF_3$ and $OCH_2CH_2Cl$.

Preference is given to haloalkyls or haloalkenyls having 1 to 4 carbon atoms and 1 to 9, preferably 1 to 5, identical or different halogen atoms selected from the group consisting of fluorine, chlorine and bromine. Particular preference is given to haloalkyls having 1 or 2 carbon atoms and 1 to 5 identical or different halogen atoms selected from the group consisting of fluorine and chlorine, such as, inter alia, difluoromethyl, trifluoromethyl, 2,2-difluoroethyl or 2,2,2-trifluoroethyl.

According to the invention, "alkylene" represents groups having 1 to 10 carbon atoms, and in particular 1 to 6 carbon atoms and preferably 2 to 4 carbon atoms, and also the corresponding unsaturated and/or substituted radicals in the carbon skeleton, which may in each case be straight-chain or branched. Examples are methylene, ethylene, n- and isopropylene and n-, s-, iso-, t-butylene.

Examples of hydroxyalkyl groups are 1,2-dihydroxyethyl and 3-hydroxypropyl.

According to the invention, "aryl"—on its own or as component of a chemical group—represents a mono-, bi- or polycyclic aromatic system having preferably 6 to 14, in particular 6 to 10, carbon ring atoms, such as, for example, phenyl, naphthyl, anthryl, phenanthrenyl, preferably phenyl. Furthermore, aryl also represents polycyclic systems, such as tetrahydronaphthyl, indenyl, indanyl, fluorenyl, biphenyl, where the binding site is at the aromatic system. The aryl groups according to the invention can be substituted by one or more identical or different radicals.

According to the invention, "heterocyclyl" or "heterocycle" represents a heterocyclic ring (=carbocyclic ring in which at least one carbon atom is replaced by a heteroatom, preferably a heteroatom from the group consisting of N, O, S, P, B, Si, Se) which is saturated, unsaturated or heteroaromatic and may be unsubstituted or substituted, where the binding site is localized at a ring atom. Unless defined otherwise, the heterocyclic ring preferably contains 3 to 9 ring atoms, in particular 3 to 6 ring atoms, and one or more, preferably 1 to 4, in particular 1, 2 or 3, heteroatoms in the heterocyclic ring, preferably from the group consisting of N, O and S, where, however, two oxygen atoms must not be directly adjacent. The heterocyclyl groups according to the invention may be substituted by one or more identical or different radicals.

If the heterocyclyl radical or the heterocyclic ring is substituted, it may be fused to other carbocyclic or heterocyclic rings. Optionally substituted heterocyclyl also comprises polycyclic systems, such as, for example, 8-azabicyclo[3.2.1]octanyl or 1-azabicyclo[2.2.1]heptyl. Optionally substituted heterocyclyl also comprises spirocyclic systems, such as, for example, 1-oxa-5-azaspiro[2,3]hexyl.

According to the invention, "heteroaryl" or "hetaryl" represents heterocyclyl groups which are heteroaromatic, i.e. represent a fully unsaturated aromatic heterocyclic compound.

According to the invention, "substituted by one or more radicals" means that, independently of one another, one or more identical or different radicals may be present as substituents. Likewise, two or more of these radicals attached to a ring system may form one or more rings, thus giving rise to condensed ring systems.

Substituted radicals, such as a substituted alkyl, alkenyl, alkynyl, cycloalkyl, cycloalkenyl, aryl, phenyl, benzyl, heterocyclyl and heteroaryl radical, are, for example, substituted radicals derived from an unsubstituted skeleton, the substituents being, for example, one or more, preferably 1, 2 or 3, radicals from the group consisting of halogen, alkoxy, alkylthio, hydroxyl, amino, nitro, carboxyl or a group equivalent to the carboxyl group, cyano, isocyano, azido, alkoxycarbonyl, alkylcarbonyl, formyl, carbamoyl, mono- and dialkylaminocarbonyl, substituted amino, such as acylamino, mono- and dialkylamino, trialkylsilyl and optionally substituted cycloalkyl, optionally substituted aryl, optionally substituted heterocyclyl, where each of the last-mentioned cyclic groups may also be attached via heteroatoms or divalent functional groups, such as in the case of the alkyl radicals mentioned, and alkylsulphinyl, where both enantiomers of the alkylsulphinyl group are included, alkylsulphonyl, alkylphosphinyl, alkylphosphonyl and, in the case of cyclic radicals (="cyclic skeleton"), also alkyl, haloalkyl, alkylthioalkyl, alkoxyalkyl, optionally substituted mono- and dialkylaminoalkyl and hydroxyalkyl; the term "substituted radicals", such as substituted alkyl, etc., includes as substituents, in addition to the saturated hydrocarbon-containing radicals mentioned, corresponding unsaturated aliphatic and aromatic radicals, such as optionally substituted alkenyl, alkynyl, alkenyloxy, alkynyloxy, alkenylthio, alkynylthio, alkenyloxycarbonyl, alkynyloxycarbonyl, alkenylcarbonyl, alkynylcarbonyl, mono- and dialkenylaminocarbonyl, mono- and dialkynylaminocarbonyl, mono- and dialkenylamino, mono- and dialkynylamino, trialkenylsilyl, trialkynylsilyl, optionally substituted cycloalkenyl, optionally substituted cycloalkynyl, phenyl, phenoxy, etc. In the case of substituted cyclic radicals having aliphatic moieties in the ring, this also includes cyclic systems having such substituents which are attached at the ring through a double bond, for example cyclic systems substituted by an alkylidene group, such as methylidene or ethylidene, or an oxo group, imino group or substituted imino group.

If two or more radicals form one or more rings, these can be carbocyclic, heterocyclic, saturated, partially saturated, unsaturated, for example also aromatic, and optionally substituted further. The fused rings are preferably 5- or 6-membered rings; particular preference is given to benzo-fused cycles.

The substituents mentioned by way of example ("first substituent level") can, if they contain hydrocarbon-containing moieties, optionally be further substituted therein ("second substituent level"), for example by one of the substituents as defined for the first substituent level. Corresponding further substituent levels are possible. Preferably, the term "substituted radical" only comprises one or two substituent levels.

Preferred substituents for the substituent levels are, for example, amino, hydroxyl, halogen, nitro, cyano, isocyanato, mercapto, isothiocyanato, carboxyl, carbonamide, $SF_5$, aminosulphonyl, alkyl, cycloalkyl, alkenyl, cycloalkenyl, alkynyl, monoalkylamino, dialkylamino, N-alkanoylamino, alkoxy, alkenyloxy, alkynyloxy, cycloalkoxy, cycloalkenyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylthio, cycloalkylthio, alkenylthio, cycloalkenylthio, alkynylthio, alkylsulphenyl, alkylsulphinyl, where both enantiomers of the alkylsulphinyl group are included, alkylsulphonyl, monoalkylaminosulphonyl, dialkylaminosulphonyl, alkylphosphinyl, alkylphosphonyl, where, for alkylphosphinyl and alkylphosphonyl, both enantiomers are included, N-alkylaminocarbonyl, N,N-dialkylaminocarbonyl, N-alkanoylaminocarbonyl, N-alkanoyl-N-alkylaminocarbonyl, aryl, aryloxy, benzyl, benzyloxy, benzylthio, arylthio, arylamino, benzylamino, heterocyclyl and trialkylsilyl.

As already mentioned, from among the radicals having carbon atoms, preference is given to those having 1 to 6 carbon atoms, preferably 1 to 4 carbon atoms, in particular 1 or 2 carbon atoms. Preference is generally given to substituents from the group consisting of halogen, for example fluorine, chlorine and bromine, $(C_1-C_4)$-alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano.

Optionally substituted aryl or heteroaryl is preferably phenyl or heteroaryl which is unsubstituted or mono- or polysubstituted, preferably up to trisubstituted, by identical or different radicals from the group consisting of halogen, $(C_1-C_4)$-alkyl, $(C_3-C_6)$-cycloalkyl, $(C_1-C_4)$-alkoxy, $(C_1-C_4)$-haloalkyl, $(C_1-C_4)$-haloalkoxy, $(C_1-C_4)$-alkylthio, cyano and nitro, for example o-, m- and p-tolyl, dimethylphenyls, 2-, 3- and 4-chlorophenyl, 2-, 3- and 4-trifluoromethyl, 2,4-, 3,5-, 2,5- and 2,3-dichlorophenyl, o-, m- and p-methoxyphenyl.

In a first embodiment, the invention relates to compounds of the general formula (IA)

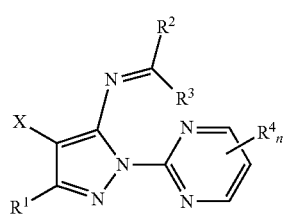

(IA)

in which n represents 0, 1, 2 or 3 and the groupings X, $R^1$, $R^2$, $R^3$ and $R^4$ have the meaning mentioned above, and to use of the compound (IA) for controlling animal pests.

In a second embodiment, the invention relates to compounds of the first embodiment in which X represents substituted phenyl which is preferably substituted by at least one substituent Y, where the substituent Y represents halogen, cyano, nitro, $C_1-C_6$-alkyl, halo-$C_1-C_6$-alkyl, $C_1-C_6$-alkoxy, $C_1-C_6$-alkoxy-$C_1-C_6$-alkyl, $C_1-C_6$-alkoxy-$C_1-C_6$-alkoxy, $C_3-C_6$-cycloalkyl, $C_2-C_6$-alkenyloxy, $C_2-C_6$-alkynyloxy, benzyl oxy, $C_3-C_6$-cycloalkyl-$C_1-C_6$-alkoxy, halo-$C_1-C_6$-alkoxy, halo-$C_1-C_6$-alkoxy-$C_1-C_6$-alkyl, $C_1-C_6$-alkylsulphanyl, halo-$C_1-C_6$-alkylsulphanyl, $C_1-C_6$-alkylsulphinyl, halo-$C_1-C_6$-alkylsulphinyl, $C_1-C_6$-alkylsulphonyl, halo-$C_1-C_6$-alkylsulphonyl, $C_1-C_6$-alkylcarbonyl, $C_1-C_6$-alkoxycarbonyl, $C_1-C_6$-alkoxycarbonyl-$C_1-C_6$-alkyl, carboxyl, carboxamide, di-$C_1-C_6$-alkylcarboxamide, tri-$C_1-C_6$-alkylsilyl, amino, $C_1-C_6$-alkylamino, di-$C_1-C_6$-alkylamino, $C_1-C_6$-alkylsulphonylamino, di-$C_1-C_6$-alkylsulphonylamino, formyl, —CH=NO—H, —CH=NO—$C_1-C_6$-alkyl, —CH=NO-halo-$C_1-C_6$-alkyl, —C(CH$_3$)=NO—H, —C(CH$_3$)=NO—$C_1-C_6$-alkyl or —C(CH$_3$)=NO-halo-$C_1-C_6$-alkyl, preferably halogen, $C_1-C_6$-haloalkyl, $C_1-C_6$-alkoxy or $C_1-C_6$-alkyl.

In a third embodiment, the invention relates to compounds of the first embodiment in which X represents substituted phenyl having at least two adjacent (vicinal) substituents Y selected from the group consisting of $C_1-C_6$-alkyl, halo-$C_1-C_6$-alkyl, $C_1-C_6$-alkoxy and halo-$C_1-C_6$-alkoxy which, together with the carbon atoms to which they are attached, form a five- or six-membered cyclic system which contains 0 to 2 oxygen or nitrogen atoms, where the carbon atoms of the cyclic system may be substituted by one or more halogen atoms and/or $C_1-C_6$-alkyl radicals; within the third embodiment, preference is given to compounds having one of the basic structures (IA-1) to (IA-5) below:

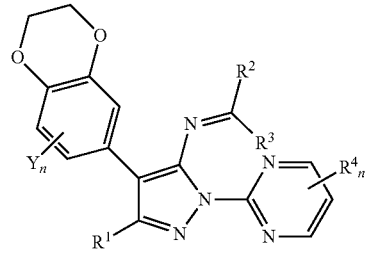

(IA-1)

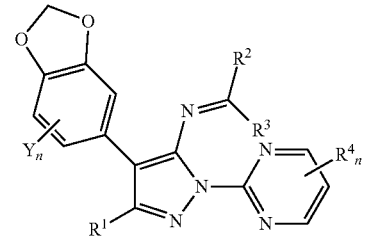

(IA-2)

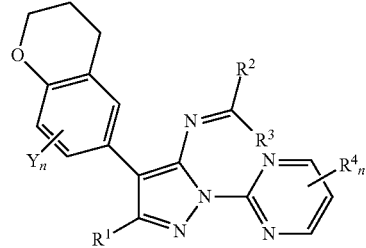

(IA-3)

-continued (IA-4)

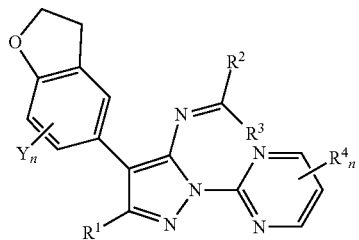

(IA-5)

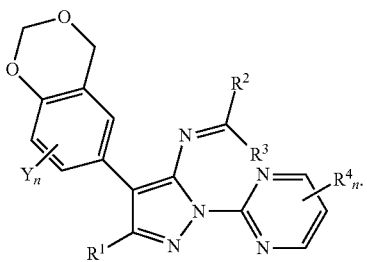

In a fourth embodiment, the invention relates to compounds of the general formula (IB)

(IB)

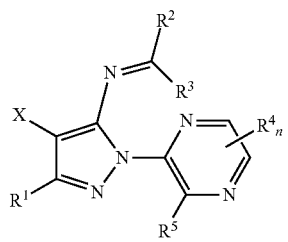

in which n represents 0, 1 or 2 and the groupings X, $R^1$, $R^2$, $R^3$, $R^4$ and $R^5$ have the meaning mentioned above, and to the use of the compound (IB) for controlling animal pests.

In a fifth embodiment, the invention relates to compounds of the fourth embodiment in which X represents substituted phenyl which is preferably substituted by at least one substituent Y, where the substituent Y represents halogen, cyano, nitro, $C_1$-$C_6$-alkyl, halo-$C_1$-$C_6$-alkyl, $C_1$-$C_6$-alkoxy, $C_1$-$C_6$-alkoxy-$C_1$-$C_6$-alkyl, $C_1$-$C_6$-alkoxy-$C_1$-$C_6$-alkoxy, $C_3$-$C_6$-cycloalkyl, $C_2$-$C_6$-alkenyloxy, $C_2$-$C_6$-alkynyloxy, benzyloxy, $C_3$-$C_6$-cycloalkyl-$C_1$-$C_6$-alkoxy, halo-$C_1$-$C_6$-alkoxy, halo-$C_1$-$C_6$-alkoxy-$C_1$-$C_6$-alkyl, $C_1$-$C_6$-alkylsulphanyl, halo-$C_1$-$C_6$-alkylsulphanyl, $C_1$-$C_6$-alkylsulphinyl, halo-$C_1$-$C_6$-alkylsulphinyl, $C_1$-$C_6$-alkylsulphonyl, halo-$C_1$-$C_6$-alkylsulphonyl, $C_1$-$C_6$-alkylcarbonyl, $C_1$-$C_6$-alkoxycarbonyl, $C_1$-$C_6$-alkoxycarbonyl-$C_1$-$C_6$-alkyl, carboxyl, carboxamide, di-$C_1$-$C_6$-alkylcarboxamide, tri-$C_1$-$C_6$-alkylsilyl, amino, $C_1$-$C_6$-alkylamino, di-$C_1$-$C_6$-alkylamino, $C_1$-$C_6$-alkylsulphonyl amino, di-$C_1$-$C_6$-alkyl sulphonylamino, formyl, alkyl, —CH=NO-halo-$C_1$-$C_6$-alkyl, —C(CH$_3$)=NO—H, —C(CH$_3$)=NO—$C_1$-$C_6$-alkyl or —C(CH$_3$)=NO-halo-$C_1$-$C_6$-alkyl, preferably halogen, $C_1$-$C_6$-haloalkyl, $C_1$-$C_6$-alkoxy or $C_1$-$C_6$-alkyl.

In a sixth embodiment, the invention relates to compounds of the fourth embodiment in which X represents substituted phenyl having at least two adjacent (vicinal) substituents Y selected from the group consisting of $C_1$-$C_6$-alkyl, halo-$C_1$-$C_6$-alkyl, $C_1$-$C_6$-alkoxy and halo-$C_1$-$C_6$-alkoxy which, together with the carbon atoms to which they are attached, form a five- or six-membered cyclic system which contains 0 to 2 oxygen or nitrogen atoms, where the carbon atoms of the cyclic system may be substituted by one or more halogen atoms and/or $C_1$-$C_6$-alkyl radicals; within the third embodiment, preference is given to compounds having one of the basic structures (IB-1) to (IB-5) below:

(IB-1)

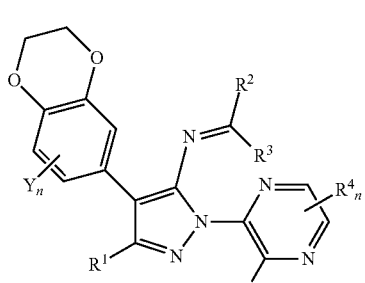

(IB-2)

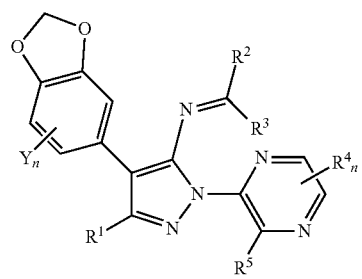

(IB-3)

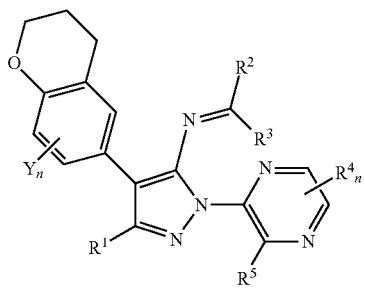

(IB-4)

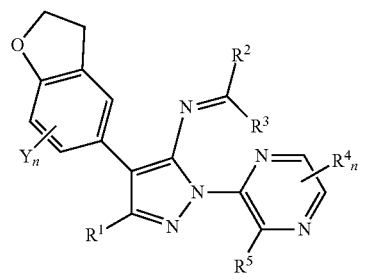

(IB-5)

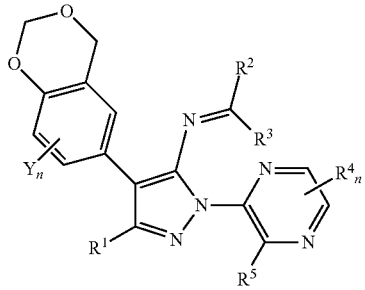

The compounds according to the invention include, if chemically possible, salts, tautomers, diastereomers and optical isomers or isomer mixtures of varying compositions. The present invention provides both the pure stereoisomers and any mixtures of these isomers. Imines and imidoates may likewise be present as pure E or Z form or as a variable mixture of E and Z form.

The present invention likewise comprises compounds according to the invention which are quaternized by protonation, alkylation or oxidation at a nitrogen atom.

Depending on the nature of the substituents defined above, the compounds according to the invention have acidic or basic properties and may form salts. If the compounds according to the invention carry hydroxyl groups, carboxyl groups or other groups which induce acidic properties, these compounds can be reacted with bases to give salts. Suitable bases are, for example, hydroxides, carbonates, bicarbonates of the alkali metals and alkaline earth metals, in particular those of sodium, potassium, magnesium and calcium, furthermore ammonia, primary, secondary and tertiary amines having $(C_1-C_4)$-alkyl radicals, and also mono-, di- and trialkanolamines of $(C_1-C_4)$-alkanoles. If the compounds according to the invention carry amino groups, alkylamino groups or other groups which induce basic properties, these compounds can be reacted with acids to give salts. Suitable acids are, for example, mineral acids, such as hydrochloric acid, sulphuric acid and phosphoric acid, organic acids, such as acetic acid or oxalic acid, and acidic salts, such as $NaHSO_4$ and $KHSO_4$. The salts which can be obtained in this manner also have insecticidal and akaricidal properties.

The present invention also provides the salt-like derivatives formed from the compounds according to the invention by reaction with basic or acidic compounds, and also the N-oxides, which can be prepared by customary oxygenation methods.

The compounds or compositions according to the invention can, as such or in their (commercial) formulations and in the use forms prepared from these formulations, be present as a mixture with further active compounds such as insecticides, herbicides and fungicides, attractants, steprilants, growth regulators, fertilizers, safeners and/or semiochemicals. Likewise, the active compounds and compositions according to the invention can be used in mixtures with agents for improving plant properties.

In a particular embodiment of the invention, the active compounds or compositions according to the invention are present in commercial formulations or in the use forms prepared from these formulations in a mixture with synergists and are employed as insecticides. Synergists are to be understood as meaning compounds which increase the activity of the active compounds according to the invention, without the synergist having any activity.

In a further particular embodiment, the compositions according to the invention are present in commercial formulations or in the use forms prepared from these formulations in mixtures with inhibitors which reduce the degradation of the agrochemical active compound contained after application in the surroundings of the plant, on the surface of plant parts or in plant tissues.

The active compounds of the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as crop protection agents. They are active against normally sensitive and resistant species and against all or some stages of development. The abovementioned pests include:

From the phylum Mollusca, for example from the class of the Lamellibranchiata, for example Dreissena spp.

From the class of the Gastropoda, for example Arion spp., Biomphalaria spp., Bulinus spp., Deroceras spp., Galba spp., Lymnaea spp., Oncomelania spp., Pomacea spp., Succinea spp.

From the phylum Arthropoda, for example from the order of the Isopoda, for example Armadillidium vulgare, Oniscus asellus, Porcellio scaber.

From the class of the Arachnida, for example Acarus spp., Aceria sheldoni, Aculops spp., Aculus spp., Amblyomma spp., Amphitetranychus viennensis, Argas spp., Boophilus spp., Brevipalpus spp., Bryobia praetiosa, Centruroides spp., Chorioptes spp., Dermanyssus gallinae, Dennatophagoides pteronyssius, Dermatophagoides farinae, Dermacentor spp., Eotetranychus spp., Epitrimerus pyri, Eutetranychus spp., Eriophyes spp., Halotydeus destructor, Hemitarsonemus spp., Hyalomma spp., Ixodes spp., Latrodectus spp., Loxosceles spp., Metatetranychus spp., Nuphersa spp., Oligonychus spp., Ornithodorus spp., Ornithonyssus spp., Panonychus spp., Phyllocoptruta oleivora, Polyphagotarsonemus latus, Psoroptes spp., Rhipicephalus spp., Rhizoglyphus spp., Sarcoptes spp., Scorpio maurus, Stenotarsonemus spp., Tarsonemus spp., Tetranychus spp., Vaejovis spp., Vasates lycopersici.

From the order of the Symphyla, for example Scutigerella spp.

From the order of the Chilopoda, for example Geophilus spp., Scutigera spp.

From the order of the Collembola, for example Onychiurus armatus.

From the order of the Diplopoda, for example Blaniulus guttulatus.

From the order of the Zygentoma, for example Lepisma saccharina, Thermobia domestica.

From the order of the Orthoptera, for example Acheta domesticus, Blatta orientalis, Blattella germanica, Dichroplus spp., Gryllotalpa spp., Leucophaea maderae, Locusta spp., Melanoplus spp., Periplaneta spp., Pulex irritans, Schistocerca gregaria, Supella longipalpa.

From the order of the Isoptera, for example Coptotermes spp., Cornitermes cumulans, Cryptotermes spp., Incisitermes spp., Microtermes obesi, Odontotermes spp., Reticulitermes spp., From the order of the Heteroptera, for example Anasa tristis, Antestiopsis spp., Boisea spp., Blissus spp., Calocoris spp., Campylomma livida, Cavelerius spp., Cimex lectularius, Collaria spp., Creontiades dilutus, Dasynus piperis, Dichelops furcatus, Diconocoris hewetti, Dysdercus spp., Euschistus spp., Eurygaster spp., Heliopeltis spp., Horcias nobilellus, Leptocorisa spp., Leptoglossus phyllopus, Lygus spp., Macropes excavatus, Miridae, Monalonion atratum, Nezara spp., Oebalus spp., Pentomidae, Piesma quadrata, Piezodorus spp., Psallus spp., Pseudacysta persea, Rhodnius spp., Sahlbergella singularis, Scaptocoris castanea, Scotinophora spp., Stephanitis nashi, Tibraca spp., Triatoma spp.

From the order of the Anoplura (Phthiraptera), for example Damalinia spp., Haematopinus spp., Linognathus spp., Pediculus spp., Ptirus pubis, Trichodectes spp.

From the order of the Homoptera, for example Acyrthosipon spp., Acrogonia spp., Aeneolamia spp., Agonoscena spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus Kalli*, *Coccus* spp., *Cryptomyzus ribis*, *Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus*, *Ferrisia* spp., *Geococcus coffeae*, *Hieroglyphus* spp., *Homalodisca coagulata*, *Hyalopterus arundinis*, *Icerya* spp., *Idiocerus* spp., *Idioscopus* spp., *Laodclphax striatellus*, *Lecanium* spp., *Lepidosaphes* spp., *Lipaphis erysimi*, *Macrosiphum* spp., *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes* spp., *Trioza* spp., *Typhlocyba* spp., *Unaspis* spp., *Viteus vitifolii*, *Zygina* spp.

From the order of the Coleoptera, for example *Acalymma vittatum*, *Acanthoscelides obtectus*, *Adoretus* spp., *Agelastica alni*, *Agriotes* spp., *Alphitobius diaperinus*, *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptorhynchus lapathi*, *Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides*, *Hellula undalis*, *Heteronychus arator*, *Heteronyx* spp., *Hylamorpha elegans*, *Hylotrupes bajulus*, *Hypera postica*, *Hypothenemus* spp., *Lachnosterna consanguinea*, *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aencus*, *Melolontha* spp., *Migdolus* spp., *Monochamus* spp., *Naupactus xanthographus*, *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllotreta* spp., *Popillia japonica*, *Premnotrypes* spp., *Prostephanus truncatus*, *Psylliodes* spp., *Ptinus* spp., *Rhizobius ventralis*, *Rhizopertha dominica*, *Sitophilus* spp., *Sphenophorus* spp., *Stegobium paniceum*, *Steprnechus* spp., *Symphyletes* spp., *Tanymecus* spp., *Tenebrio molitor*, *Tribolium* spp., *Trogoderma* spp., *Tychius* spp., *Xylotrechus* spp., *Zabrus* spp.

From the order of the Hymenoptera, for example *Acromyrmex* spp., *Athalia* spp., *Atta* spp., *Diprion* spp., *Hoplocampa* spp., *Lasius* spp., *Monomorium pharaonic*, *Solenopsis invicta*, *Tapinoma* spp., *Vespa* spp.

From the order of the Lepidoptera, for example *Acronicta major*, *Adoxophyes* spp., *Aedia leucomelas*, *Agrotis* spp., *Alabama* spp., *Amyelois transitella*, *Anarsia* spp., *Anticarsia* spp., *Argyroploce* spp., *Barathra brassicae*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pomonella*, *Carposina niponensis*, *Chematobia brumata*, *Chilo* spp., *Choristoneura* spp., *Clysia ambiguella*, *Cnaphalocerus* spp., *Cnephasia* spp., *Conopomorpha* spp., *Conotrachelus* spp., *Copitarsia* spp., *Cydia* spp., *Dalaca noctuides*, *Diaphania* spp., *Diatraea saccharalis*, *Earias* spp., *Ecdytolopha aurantium*, *Elasmopalpus lignosellus*, *Eldana saccharina*, *Ephestia* spp., *Epinotia* spp., *Epiphyas postvittana*, *Etiella* spp., *Eulia* spp., *Eupoecilia ambiguella*, *Euproctis* spp., *Euxoa* spp., *Feltia* spp., *Galleria mellonella*, *Gracillaria* spp., *Grapholitha* spp., *Hedylepta* spp., *Helicoverpa* spp., *Heliothis* spp., *Hofmannophila pseudospretella*, *Homoeosoma* spp., *Homona* spp., *Hyponomeuta padella*, *Kakivoria flavofasciata*, *Laphygma* spp., *Laspeyresia molesta*, *Leucinodes orbonalis*, *Leucoptera* spp., *Lithocolletis* spp., *Lithophane antennata*, *Lobesia* spp., *Loxagrotis albicosta*, *Lymantria* spp., *Lyonetia* spp., *Malacosoma neustria*, *Maruca testulalis*, *Mamestra brassicae*, *Mocis* spp., *Mythimna separata*, *Nymphula* spp., *Oiketicus* spp., *Oria* spp., *Orthaga* spp., *Ostrinia* spp., *Oulema oryzae*, *Panolis flammea*, *Parnara* spp., *Pectinophora* spp., *Perileucoptera* spp., *Phthorimaea* spp., *Phyllocnistis citrella*, *Phyllonorycter* spp., *Pieris* spp., *Platynota stultana*, *Plodia interpunctella*, *Plusia* spp., *Plutella xylostella*, *Prays* spp., *Prodenia* spp., *Protoparce* spp., *Pseudaletia* spp., *Pseudoplusia includens*, *Pyrausta nubilalis*, *Rachiplusia nu*, *Schoenobius* spp., *Scirpophaga* spp., *Scotia segetum*, *Sesamia* spp., *Sparganothis* spp., *Spodoptera* spp., *Stathmopoda* spp., *Stomopteryx subsecivella*, *Synanthedon* spp., *Tecia solanivora*, *Thermesia gemmatalis*, *Tinea pellionella*, *Tineola bisselliella*, *Tortrix* spp., *Trichophaga tapetzella*, *Trichoplusia* spp., *Tuta absoluta*, *Virachola* spp.

From the order of the Diptera, for example *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Ceratitis capitata*, *Chironomus* spp., *Chrysomyia* spp., *Chrysops* spp., *Cochliomyia* spp., *Contarinia* spp., *Cordylobia anthropophaga*, *Culex* spp., *Culicoides* spp., *Culiseta* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gasterophilus* spp., *Glossina* spp., *Haematopota* spp., *Hydrellia* spp., *Hylemyia* spp., *Hyppobosca* spp., *Hypoderma* spp., *Liriomyza* spp. *Lucilia* spp., *Lutzomia* spp., *Mansonia* spp., *Musca* spp., *Nezara* spp., *Oestrus* spp., *Oscinella frit*, *Pegomyia* spp., *Phlebotomus* spp., *Phorbia* spp., *Phormia* spp., *Prodiplosis* spp., *Psila rosae*, *Rhagoletis* spp., *Sarcophaga* spp., *Simulium* spp., *Stomoxys* spp., *Tabanus* spp., *Tannia* spp., *Tetanops* spp., *Tipula* spp.

From the order of the Thysanoptera, for example *Anaphothrips obscurus*, *Baliothrips biformis*, *Drepanothris reuteri*, *Enneothrips flavens*, *Frankliniella* spp., *Heliothrips* spp., *Hercinothrips femoralis*, *Rhipiphorothrips cruentatus*, *Scirtothrips* spp., *Taeniothrips cardamoni*, *Thrips* spp.

From the order of the Siphonaptera, for example *Ceratophyllus* spp., *Ctenocephalides* spp., *Tunga penetrans*, *Xenopsylla cheopis*.

From the phyla of the Plathelminthes and Nematodes as animal parasites, for example from the class of the Helminthes, for example *Ancylostoma duodenale*, *Ancylostoma*

*ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp, *Strongyloides fuellebomi, Strongyloides stercoralis, Strongyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

From the phylum of the Nematodes as plant pests, for example *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

From the subphylum of the Protozoa, for example *Eimeria*.

To achieve the desired effect in crop protection, in general, plants and plant parts are treated with the compounds according to the invention, i.e. active compounds and compositions, directly or by action on their surroundings, habitat or storage space by the customary treatment methods, for example by dipping, spraying, atomizing, irrigating, evaporating, dusting, fogging, broadcasting, foaming, painting, spreading, drenching, drip irrigating and, in the case of propagation material, especially in the case of seed, additionally by seed dressing, wet seed dressing, slurry seed dressing, by encrusting, by coating with one or more coats, etc. It is furthermore possible to apply the active compounds by the ultra-low volume method, or to inject the active compound preparation or the active compound itself into the soil.

A preferred direct treatment of the plants is folio application, i.e. active compounds, active compound combinations or compositions according to the invention are applied to the foliage, in which case it is possible to adjust the treatment frequency and the application rate to the infestation pressure of the particular pathogen, insect, weed.

In the case of systemically active compounds, the active compounds, active compound combinations or compositions according to the invention get into the plants via the root structure. In that case, the plants are treated by the action of the active compounds, active compound combinations or compositions according to the invention on the habitat of the plant. This can be done, for example, by drenching, i.e. the site of the plant (for example the soil or hydroponic systems) is drenched with a liquid form of the active compounds, active compound combinations or compositions according to the invention, or by soil application, i.e. the active compounds, active compound combinations or compositions according to the invention are introduced into the site of the plants in solid form (for example in the form of granules). In the case of paddy rice crops, this may also be accomplished by metered addition of the invention in a solid application form (for example as granules) into a flooded paddy field.

Plants are to be understood as meaning all plant species, plant cultivars and plant populations such as wanted and unwanted wild plants or crop plants. Crop plants to be treated according to the invention are plants which occur naturally, or those which have been obtained by conventional breeding and optimization methods or by biotechnological and genetic engineering methods or by combinations of the aforementioned methods. The term crop plant of course also encompasses transgenic plants.

Plant cultivars are understood as meaning plants with new properties, so-called traits, which have been cultivated either by conventional breeding, by mutagenesis or by recombinant DNA techniques or a combination thereof. These can be cultivars, strains, bio- and genotypes.

Plant parts are to be understood as meaning all parts and organs of the plants above and below the ground, such as shoot, leaf, flower and root, in particular leaves, needles, stalks, stems, flowers, fruit bodies, fruits, seeds, roots, tubers and rhizomes. Furthermore, the term plant parts encompasses harvested material and also vegetative and generative propagation material, such as, for example, cuttings, tubers, rhizomes, offshoots and seeds or seed material.

In one embodiment of the invention, plant species and plant cultivars which are naturally occurring or have been obtained by conventional breeding and optimization methods (for example hybridization or protoplast fusion), and plant parts thereof, are treated.

In a further embodiment of the invention, transgenic plants which have been obtained by genetic engineering methods, if appropriate in combination with conventional methods, and parts thereof, are treated.

The present invention furthermore relates to a method for protecting seed and germinating plants against attack by pests by treating the seed with the compounds or compositions according to the invention.

The invention also relates to the use of the compounds or compositions according to the invention for treating seed for protecting the seed and the plant originating therefrom against pests. Furthermore, the invention relates to seed treated with compounds or compositions according to the invention for protection against pests. One of the advantages of the present invention is, that, by virtue of the particular systematic properties of the compounds or compositions according to the invention, the treatment of the seed with these compounds or compositions protects not only the seed itself, but also the resulting plants after emergence, from pests. In this manner, the immediate treatment of the crop at the time of sowing or shortly thereafter can be dispensed with.

It must also be considered as advantageous that the compounds or compositions according to the invention can also be employed in particular in transgenic seed, the plants arising from this seed being capable of expressing a protein directed against pests. By treating such seed with the compounds or compositions according to the invention, certain pests can be controlled merely by the expression of the, for example, insecticidal protein, and additionally damage to the seed may be averted by the active compound combinations according to the invention.

The compounds or compositions according to the invention are suitable for protecting seed of any plant cultivar as already mentioned above which is employed in agriculture, in the greenhouse, in forests or in horticulture. In particular, this takes the form of seed of maize, peanut, canola, oilseed rape, poppy, soya beans, cotton, beet (for example sugar beet and fodder beet), rice, millet, wheat, barley, oats, rye, sunflower, tobacco, potatoes or vegetables (for example tomatoes, cabbage species). The compounds or compositions according to the invention are likewise suitable for treating the seed of fruit plants and vegetables as already mentioned above. The treatment of the seed of maize, soya beans, cotton, wheat and canola or oilseed rape is of particular importance.

As already mentioned above, the treatment of transgenic seed with compounds or compositions according to the invention is also of particular importance. This takes the form of seed of plants which, in general, comprise at least one heterologist gene which controls the expression of a polypeptide with in particular insecticidal properties. In this context, the heterologist genes in transgenic seed may be derived from microorganisms such as *Bacillus, Rhizobium, Pseudomonas, Serratia, Trichoderma, Clavibacter, Glomus* or *Gliocladium*. The present invention is particularly suitable for the treatment of transgenic seed which comprises at least one heterologist gene originating from *Bacillus* sp. and whose gene product shows activity against the European corn borer and/or the corn root worm. It is particularly preferably a heterologist gene derived from *Bacillus thuringiensis*.

The transgenic plants or plant cultivars which are preferably treated according to the invention include all plants which, in the genetic modification, received genetic material which imparts particularly advantageous useful traits to these plants. Examples of such traits are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are particularly emphasized are the increased defence of the plants against insects, arachnids, nematodes and gastropods by toxins formed in the plants, in particular those formed in the plants by the genetic material from *Bacillus thuringiensis* (for example by the genes CryIA(a), CryIA(b), CryIA(c), CryllA, CryIIIA, CryIIIB2, Cry9c Cry2Ab, Cry3Bb and CryIF and also combinations thereof) (hereinbelow referred to as "Bt plants"). Traits that are also particularly emphasized are the increased defence of plants against fungi, bacteria and viruses by systemic acquired resistance (SAR), systemin, phytoalexins, elicitors and also resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes in question which impart the desired traits can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya bean), KnockOut® (for example maize), StarLink® (for example maize), Bollgard® (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these or still-to-be-developed genetic traits, which plants will be developed and/or marketed in the future.

In addition to the use of the compounds or compositions according to the invention in crop protection, in particular for controlling a large number of different pests including, for example, harmful sucking insects, biting insects and other pests which are parasites on plants, the compounds or compositions according to the invention can, as mentioned above, be used for controlling storage pests, pests which destroy industrial materials and hygiene pests including parasites in animal health and be employed for their control such as, for example, their elimination and destruction. Accordingly, the present invention also includes a method for controlling pests.

In particular by virtue of their strong insecticidal action, the compounds or compositions according to the invention can be used in the protection of materials for protecting industrial materials against attack and destruction by insects, such as, for example, termites. Accordingly, the invention relates to the use of the active compounds or compositions for protecting industrial materials against attack or destruction by insects. These insects include, for example, beetles, such as *Hylotrupes bajulus, Chlorophorus pilosis, Anobium punctatum, Xestobium rufovillosum, Ptilinus pecticornis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;* hymenopterans, such as *Sirex juvencus, Urocerus gigas, Urocerus gigas taignus, Urocerus augur;* termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;* bristle tails, such as *Lepisma saccharina.*

Industrial materials are to be understood as meaning, in the present context, non-living materials, such as, preferably, synthetic materials, glues, sizers, paper and board, leather, wood and timber products, and paint. The use of the invention for protecting wood is particularly preferred.

The compounds or compositions according to the invention are likewise suitable for protecting objects, in particular ship and boat hulls, sieves, nets, buildings, quays and signalling systems, which come into contact with salt water or brackish water, against being overgrown. The active compounds and compositions according to the invention, on their own or in combination with other active compounds, can also be used as antifouling agents.

In the hygiene field, i.e. in the control of hygiene pests, the compounds or compositions are preferably employed for domestic protection, hygiene protection and protection of stored products, in particular for controlling insects, arachnids and mites which are found in enclosed spaces, such as, for example, dwellings, factory halls, offices, vehicle cabins. For the control, the active compounds or compositions are used on their own or in combination with other active compounds and/or auxiliaries. They are preferably employed in domestic insecticide products. The active compounds according to the invention are active against sensitive and resistant species and against all stages of development.

These pests include, for example:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga camaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Pemphigus* spp., *Phylloera vastatrix, Phthirus pubis*.

From the order of the Heteroptera, for example, *Cimex hemipterus, Cimex lectularius, Rhodinus prolixus, Triatoma infestans*.

The use of the invention as domestic insecticide is carried out on its own or in combination with other suitable active compounds, such as phosphoric esters, carbamates, pyrethroides, neonicotinoides, growth regulators or active compounds from other known classes of insecticides.

Application is, for example, in aerosols, pressure-free spray products, for example pump and atomizer sprays, automatic fogging systems, foggers, foams, gels, evaporator products with evaporator tablets made of cellulose or synthetic material, liquid evaporators, gel and membrane evaporators, propeller-driven evaporators, energy-free, or passive, evaporation systems, moth papers, moth bags and moth gels, as granules or dusts, in bates for spraying or in bate stations.

In the animal health field, i.e. in the field of veterinary medicine, the active compounds according to the present invention are active against animal parasites, in particular ectoparasites or endoparasites. The term endoparasites includes in particular helminths, such as cestodes, nematodes or trematodes, and protozoae, such as coccidia. Ectoparasites are typically and preferably arthropods, in particular insects such as flies (stinging and licking), parasitic fly larvae, lice, hair lice, bird lice, fleas and the like; or acarids, such as ticks, for examples hard ticks or soft ticks, or mites, such as scab mites, harvest mites, bird mites and the like.

These parasites include:

from the order of the Anoplurida, for example *Haematopinus* spp., *Linognathus* spp., *Pediculus* spp., *Phtirus* spp., *Solenopotes* spp.; particular examples are: *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis, Solenopotes capillatus;* from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; particular examples are: *Bovicola bovis, Bovicola ovis, Bovicola limbata, Damalina bovis, Trichodectes canis, Felicola subrostratus, Bovicola caprae, Lepikentron ovis, Werneckiella equi;* from the order of the Diptera and the suborders Nernatocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; particular examples are: *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus,*

*Dermatobia hominis, Melophagus ovinus, Lipoptena capreoli, Lipoptena cervi, Hippobosca variegata, Hippobosca equina, Gasterophilus intestinalis, Gasterophilus haemorrhoidalis, Gasterophilus inermis, Gasterophilus nasalis, Gasterophilus nigricornis, Gasterophilus pecorum, Braula coeca;* from the order of the Siphonapterida, for example *Pulex* spp., *Ctenocephalides* spp., *Tunga* spp., *Xenopsylla* spp., *Ceratophyllus* spp.; particular examples are: *Ctenocephalides canis, Ctenocephalides felis, Pulex irritans, Tunga penetrans, Xenopsylla cheopis;* from the order of the Heteropterida, for example *Cimex* spp., *Triatoma* spp., *Rhodnius* spp., *Panstrongylus* spp.

from the order of the Blattarida, for example *Blatta orientalis, Periplaneta americana, Blattela germanica, Supella* spp. (e.g. *Suppella longipalpa);* from the subclass of the Acari (Acarina) and the orders of the Meta- and Mesostigmata, for example *Argas* spp., *Ornithodorus* spp., *Otobius* spp., *Ixodes* spp., *Amblyomma* spp., *Rhipicephalus (Boophilus)* spp *Dermacentor* spp., *Haemophysalis* spp., *Hyalomma* spp., *Dermanyssus* spp., *Rhipicephalus* spp. (the original genus of multi-host ticks) *Ornithonyssus* spp., *Pneumonyssus* spp., *Raillietia* spp., *Pneumonyssus* spp., *Sternostoma* spp., *Varroa* spp., *Acarapis* spp.; particular examples are: *Argas persicus, Argas reflexus, Ornithodorus moubata, Otobius megnini, Rhipicephalus (Boophilus) microplus, Rhipicephalus (Boophilus) decoloratus, Rhipicephalus (Boophilus) annulatus, Rhipicephalus (Boophilus) calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni;* from the order of the Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; particular examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae caprae), Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi.*

The active compounds according to the invention are also suitable for controlling arthropods, helminths and protozoae, which attack animals. Animals include agricultural livestock such as, for example, cattle, sheep, goats, horses, pigs, donkeys, camels, buffaloes, rabbits, chickens, turkeys, ducks, geese, cultured fish, honeybees. Moreover, animals include domestic animals—also referred to as companion animals—such as, for example, dogs, cats, cage birds, aquarium fish and what are known as experimental animals such as, for example, hamsters, guinea pigs, rats and mice.

By controlling these arthropods, helminths and/or protozoae, it is intended to reduce deaths and improve performance (in the case of meat, milk, wool, hides, eggs, honey and the like) and health of the host animal, so that more economical and simpler animal keeping is made possible by the use of the active compounds according to the invention.

For example, it is desirable to prevent or interrupt the uptake of blood by the parasites from the host (when applicable). Also, controlling the parasites may help to prevent the transmittance of infectious agents.

The term "controlling" as used herein with regard to the animal health field, means that the active compounds are effective in reducing the incidence of the respective parasite in an animal infected with such parasites to innocuous levels. More specifically, "controlling", as used herein, means that the active compound is effective in killing the respective parasite, inhibiting its growth, or inhibiting its proliferation.

Generally, when used for the treatment of animals, the active compounds according to the invention can be applied directly. Preferably they are applied as pharmaceutical compositions which may contain pharmaceutically acceptable excipients and/or auxiliaries which are known in the art.

In the animal health field and in animal keeping, the active compounds are applied (=administered) in the known manner by enteral administration in the form of, for example, tablets, capsules, drinks, drenches, granules, pastes, boluses, the feed-through method, suppositories; by parenteral administration, such as, for example, by injections (intramuscular, subcutaneous, intravenous, intraperitoneal and the like), implants, by nasal application, by dermal application in the form of, for example, bathing or dipping, spraying, pouring-on and spotting-on, washing, dusting, and with the aid of active-compound-comprising shaped articles such as collars, ear tags, tail tags, limb bands, halters, marking devices and the like. The active compounds may be formulated as shampoo or as suitable formulations usable in aerosols or unpressurized sprays, for example pump sprays and atomizer sprays.

When used for livestock, poultry, domestic animals and the like, the active compounds according to the invention can be applied as formulations (for example powders, wettable powders ["WP"], emulsions, emulsifiable concentrates ["EC"], flowables, homogeneous solutions, and suspension concentrates ["SC"]) which comprise the active compounds in an amount of from 1 to 80% by weight, either directly or after dilution (e.g. 100- to 10 000-fold dilution), or else as a chemical bath.

When used in the animal health field the active compounds according to the invention may be used in combination with suitable synergists or other active compounds, such as for example, acaricides, insecticides, anthelmintics and anti-protozoal drugs.

The present invention further provides formulations and application forms prepared from them (crop protection compositions or pesticide compositions) comprising at least one of the active compounds of the invention. The insecticidal formulations or application forms in question are preferably those which comprise auxiliaries, such as extenders, solvents and carriers, for example, and/or other auxiliaries, such as surface-active substances, for example.

Examples of customary formulations include solutions, emulsions, wettable powders, water-based and oil-based suspensions, water-based and oil-based suspension concentrates, powders, dusting products, pastes, soluble powders, granules, dispersible granules, soluble granules, granules for broadcasting, suspension-emulsion concentrates, natural materials impregnated with active compound, synthetic materials impregnated with active compound, fertilizers and ultra-fine encapsulations in polymeric compounds.

These formulations are produced in a conventional manner, for example by mixing of the active compounds with auxiliaries such as extenders, solvents and/or solid carriers, for example, and/or other auxiliaries such as surface-active substances, for example. The formulations are produced either in suitable equipment or else before or during application.

Auxiliaries used may be substances capable of giving the formulation of the active compound, or the application forms prepared from these formulations (such as ready-to-use crop protection compositions, for example, such as spray liquors or seed dressings) particular properties, such as certain physical, technical and/or biological properties.

Examples of suitable extenders include water, polar and non-polar organic chemical liquids, such as those, for example, from the classes of aromatic and non-aromatic hydrocarbons (such as paraffins, alkylbenzenes, alkylnaphthalenes, chlorobenzenes), alcohols and polyols (which if desired may also be substituted, etherified and/or esterified), ketones (such as acetone, cyclohexanone), esters (including fats and oils) and (poly)ethers, simple and substituted amines, amides, lactams, (such as N-alkylpyrrolidones) and lactones, sulphones and sulphoxides (such as dimethyl sulphoxide).

Where water is utilized as an extender, organic solvents as well may be used as auxiliary solvents. Liquid solvents contemplated are essentially as follows: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, such as petroleum fractions, mineral and vegetable oils, alcohols, such as butanol or glycol and their ethers and esters, ketones, such as acetone, methyl ethyl ketone, methyl isobutyl ketone or cyclohexanone, strongly polar solvents such as dimethylformamide and dimethyl sulphoxide, and also water.

In principle it is possible to use all suitable solvents. Examples of suitable solvents are aromatic hydrocarbons, such as xylene, toluene or alkylnaphthalenes, chlorinated aromatic or chlorinated aliphatic hydrocarbons, such as chlorobenzene, chloroethylene or methylene chloride, aliphatic hydrocarbons, such as cyclohexane, paraffins, petroleum fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and water.

In principle it is possible to use all suitable carriers. Carriers contemplated are more particularly the following: for example, ammonium salts and natural, finely ground minerals, such as kaolins, aluminas, talc, chalk, quartz, attapulgite, montmorillonite or diatomaceous earth, and synthetic, finely ground minerals, such as highly disperse silica, alumina and natural or synthetic silicates, resins, waxes and/or solid fertilizers. Mixtures of such carriers may likewise be used. Carriers contemplated for granules include the following: for example, crushed and fractionated natural minerals such as calcite, marble, pumice, sepiolite, dolomite, and also synthetic granules of finely ground organic and inorganic substances, and also granules of organic material such as sawdust, paper, coconut shells, maize cobs and tobacco stalks.

Liquefied gaseous extenders or solvents can also be used. Suitability is possessed more particularly by those extenders or carriers which are gaseous at standard temperature and under atmospheric pressure, examples being aerosol propellants, such as halogenated hydrocarbons, and also butane, propane, nitrogen and carbon dioxide.

Surface-active substances for the purposes of the invention are emulsifiers and/or foam formers, dispersants or wetting agents having ionic or nonionic properties, or mixtures of these surface-active substances. Examples thereof are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyltaurates), phosphoric esters of polyethoxylated alcohols or phenols, fatty acid esters of polyols, and derivatives of compounds comprising sulphates, sulphonates and phosphates, e.g. alkylaryl polyglycol ethers, alkylsulphonates, alkyl sulphates, arylsulphonates, protein hydrolysates, lignin-sulphite waste liquors and methylcellulose. The presence of a surface-active substance is advantageous if one of the active compounds and/or one of the inert carriers is insoluble in water and if application takes place in water.

Further auxiliaries present in the formulations and the application forms derived from them may include colorants, such as inorganic pigments, examples being iron oxide, titanium oxide and Prussian Blue, and organic dyes, such as alizarin dyes, azo dyes and metal phthalocyanine dyes, and nutrients, including trace nutrients, such as salts of iron, manganese, boron, copper, cobalt, molybdenum and zinc.

Additionally present may be stabilizers such as low-temperature stabilizers, preservatives, antioxidants, light stabilizers or other agents which enhance the chemical and/or physical stability. Additionally present may be foam formers or defoamers.

The formulations and application forms derived therefrom may further comprise, as additional auxiliaries, stickers such as carboxymethylcellulose, natural and synthetic polymers in powder, granule or latex form, such as gum arabic, polyvinyl alcohol, polyvinyl acetate, and also natural phospholipids, such as cephalins and lecithins, and synthetic phospholipids. Other possible auxiliaries include mineral and vegetable oils.

If desired there may also be further auxiliaries present in the formulations and in the application forms derived from them. Examples of such adjuvants include fragrances, protective colloids, binders, adhesives, thickeners, thixotropic agents, penetrants, retention promoters, stabilizers, sequestrants and complexing agents. Generally speaking, the active compounds may be combined with any solid or liquid adjuvant which is commonly used for formulation purposes.

The formulations contain preferably between 0.00000001% and 98% by weight of active compound or, with particular preference, between 0.01% and 95% by weight of active compound, more preferably between 0.5% and 90% by weight of active compound, based on the weight of the formulation. In the above context the term "active compound" also includes active compound combinations.

The active compound content of the application forms (crop protection compositions) prepared from the formulations may vary within wide ranges. The active compound concentration of the application forms may typically be between 0.00000001% and 95% by weight of active compound, preferably between 0.00001% and 1% by weight, based on the weight of the application form. In the above context, the term "active compound" also includes active compound combinations.

Application is made in a customary manner which is adapted to the application forms.

The precursors for the compounds according to the invention can be prepared analogously to the processes described in WO 2008/077483, for example in accordance with the process shown in the reaction scheme below:

inorganic acid as catalyst. Suitable acids are hydrochloric acid, sulphonic acids or acetic acid. The chlorinated ketonitriles (IID) can be reacted in the presence of a suitable base, for example an organic amine, with pyrimidinyl- or pyrazinylhydrazines of the general formula (III), to afford the aminopyrazole of the general formula (V) directly.

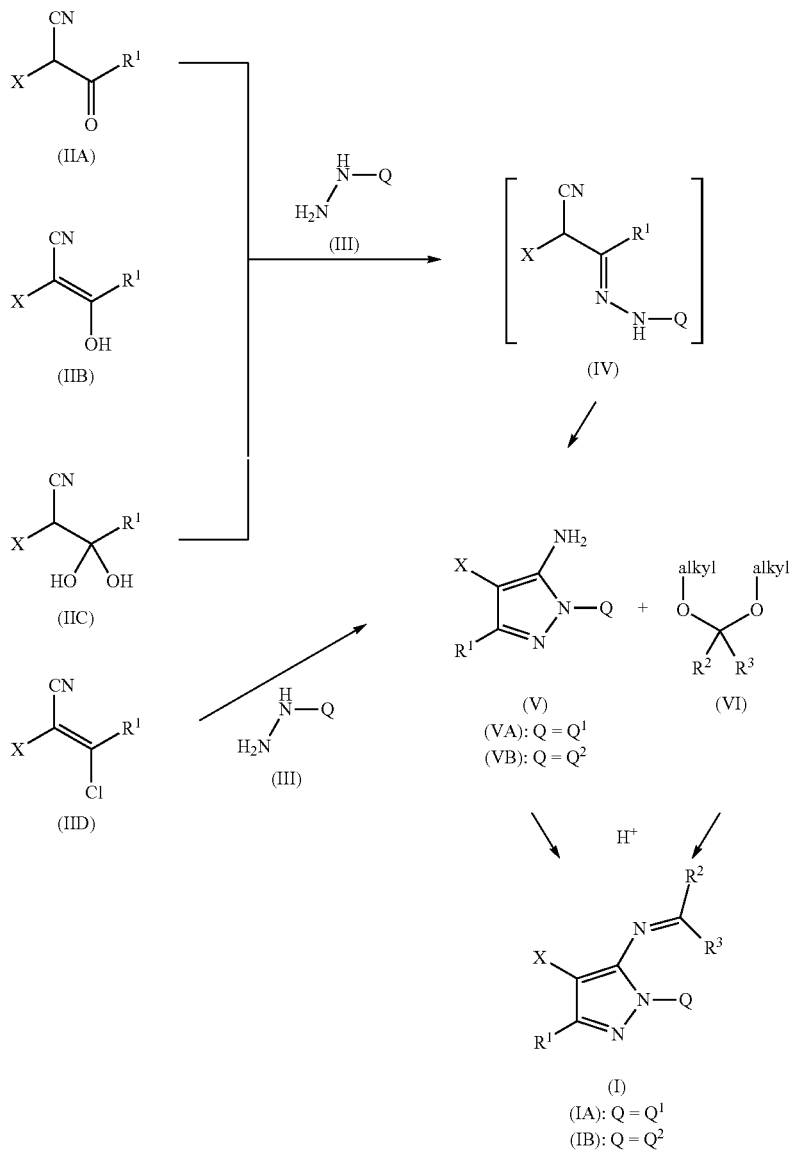

In this process for preparing the compounds according to the invention, in a first step, ketonitriles of the formulae (IIA), (IIB) or their hydrates (IIC) in which X and $R^1$ have the meanings mentioned above are reacted with pyrimidinyl- or pyrazinylhydrazines of the general formula (III) in which Q represents $Q^1$ or $Q^2$ in a condensation reaction to give a hydrazone of the general formula (IV). The ketonitriles can be present in the tautomeric forms (IIA) and (IIB) and as hydrate (IIC) and be employed in the condensation reaction of the first step. With prolonged reaction time and at elevated temperature, in particular at the boiling point of the reaction mixture, there is cyclization to the aminopyrazole of the general formula (V), if appropriate in the presence of an organic or In a second step, the aminopyrazoles (V) are reacted with ketals or orthoesters of the general formula (VI) in which $R^2$ and $R^3$ have the meanings mentioned above and "alkyl" represents methyl or ethyl, if appropriate in the presence of a catalytic amount of organic or inorganic acid (for example p-toluenesulphonic acid, acetic acid, trifluoroacetic acid, hydrochloric acid) in a suitable solvent (for example toluene, methanol or ethanol) or, if orthoesters are used, also in the absence of a solvent.

The reaction of aminopyrazoles with orthoesters can be carried out analogously to the processes known from the literature (cf. Bioorganic & Medicinal Chemistry Letters, 4(21), 2539-2544; 1994; European Journal of Medicinal Chemistry, 28(7-8), 569-756; 1993; Synthesis, (3), 242-244; 1988; and Journal of Organic Chemistry, 53(2), 382-386; 1988).

The reaction of aminopyrazoles with dimethylformamide dimethyl acetal can be carried out analogously to the processes known from the literature (US-A-2006/0014802; Bioorganic & Medicinal Chemistry Letters, 18, 2008 (3), 959-962).

The starting materials of the general formulae (IIA) and (IIB) and (III) can also be employed in the form of their salts; for example, the ketonitriles can be used in the form of their alkali metal salts and the pyrimidinyl- or pyrazinylhydrazines can be used in the form of their hydrochlorides.

Ketonitriles of the formula (II) can be prepared by the method described in W. R. Nes, Alfred Burger, J. Amer. Chem. Soc. 72 (1950), 5409-5413.

Some pyrimidinyl- or pyrazinylhydrazines of the formula (III) are commercially available. The preparation of pyrimidinyl- or pyrazinylhydrazines of the formula (III) is carried out, for example, by the methods described in Methoden der Organischen Chemie [Methods of Organic Chemistry] (Houben-Weyl), Organische Stickstoff-Verbindungen [Organic Nitrogen Compounds], Volume E 16a, part 1, pp. 678-775, Georg Thieme Verlag Stuttgart—New York, 1990; WO1998/32739 A or Journal of the Chemical Society (1955), 3478-3481.

The preparation and the use of the compounds according to the invention is illustrated by the examples below, but the invention is not limited to these examples.

A. SYNTHESIS EXAMPLES

A.1 Preparation of N'-[4-(3-bromo-5-chlorophenyl)-1-(pyrimidin-2-yl)-3-(trifluoromethyl)-1H-pyrazol-5-yl]-N,N-dimethylimidoformamide (Compound 1-91)

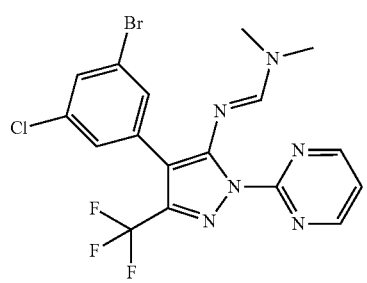 [SMILES: CN(C)/C=N/c1c(-c2cc(Cl)cc(Br)c2)c(C(F)(F)F)nn1-c1ncccn1]

1.19 g (2.84 mmol) of 4-(3-bromo-5-chlorophenyl)-1-(pyrimidin-2-yl)-3-(trifluoromethyl)-1H-pyrazol-5-amine (known from WO 2008/077843 A) and 0.51 g (4.26 mmol) of dimethylformamide dimethyl acetal are dissolved in 20 ml of toluene and stirred under reflux for 18 hours. After cooling, the toluene solution is washed with water, the organic phase is separated off, dried with magnesium sulphate and filtered and the filtrate is concentrated under reduced pressure using a rotary evaporator. The residue is stirred with a solvent mixture of cyclohexane and ethyl acetate (vol. 1:1) and the precipiated solid is filtered off and air-dried. This gives 0.99 g (67% of theory) of the compound N'-[4-(3-bromo-5-chlorophenyl)-1-(pyrimidin-2-yl)-3-(trifluoromethyl)-1H-pyrazol-5-yl]-N,N-dimethylimidoformamide.

LC-MS*: MH+=473.0; 474.9; logP=3.71

$^1$H-NMR (400 MHz, d$_6$-DMSO), δ 8.94 (d, 2H), 7.64-7.61 (m, 3H), 7.55 (s, 1H), 7.45 (s, 1H), 2.86 (br s, 3H), 2.78 (br s, 3H).

A.2 Preparation of isopropyl {4-[3-chloro-5-(trifluoromethyl)phenyl]-1-(pyrimidin-2-yl)-3-(trifluoromethyl)-1H-pyrazol-5-yl}imidoformate (Compound 1-13)

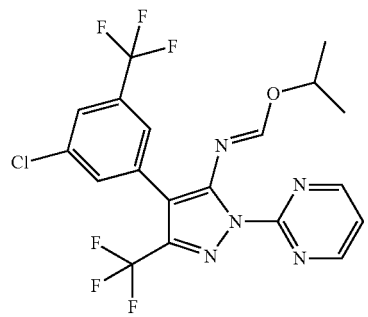 [SMILES: CC(C)O/C=N/c1c(-c2cc(Cl)cc(C(F)(F)F)c2)c(C(F)(F)F)nn1-c1ncccn1]

100 mg (0.24 mmol) of 4-[3-chloro-5-(trifluoromethyl)phenyl]-1-(pyrimidin-2-yl)-3-(trifluoromethyl)-1H-pyrazol-5-amine (known from WO 2008/077843 A) and 93.3 mg (0.48 mmol) of triisopropyl orthoformate are dissolved in 3 ml of toluene and stirred under reflux for 30 hours. The reaction solution is applied to silica gel and purified by flash chromatography on a commercial silica gel cartridge using a cyclohexane/ethyl acetate gradient. This gave 85 mg (73.6% of theory) of isopropyl {-4-[3-chloro-5-(trifluoromethyl)phenyl]-1-(pyrimidin-2-yl)-3-(trifluoromethyl)-1H-pyrazol-5-yl}imidoformate.

LC-MS**: MH+=478.1; logP=4.88

$^1$H-NMR (400 MHz, CD$_3$CN), δ 8.86 (d, 2H), 7.76-7.64 (3×s, 1 br s, 4H), 7.48 (t, 1H), 5.06-4.99 (br m, 1H), 1.19 (br s, 6H).

A.3 Preparation of 1-(3-methoxypyrazin-2-yl)-N-phenylmethylene-4-(3,4,5-trichlorochenyl)-3-(trifluoromethyl)-1H-pyrazol-5-amine (Compound 2-15)

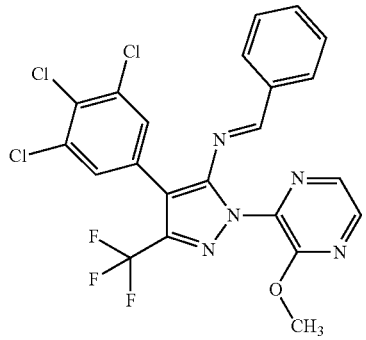 [SMILES: COc1nccnc1-n1nc(C(F)(F)F)c(-c2cc(Cl)c(Cl)c(Cl)c2)c1/N=C/c1ccccc1]

214 mg (1.4 mmol) of dimethoxymethylbenzene in 2 ml of toluene are added to 154 mg (0.35 mmol) of 1-(3-methoxypyrazin-2-yl)-4-(3,4,5-trichlorophenyl)-3-(trifluoromethyl)-1H-pyrazol-5-amine (known from EP 09161568, filing date May 5, 2009), and the mixture is stirred under reflux for 18 hours. After cooling of the reaction mixture, the volatile components are removed under reduced pressure on a rotary evaporator. The residue is stirred with a solvent mixture of cyclohexane and ethyl acetate (vol. 1:1) and sonicated in an ultrasonic bath, and the crystallized solid is filtered off with suction and air-dried. This gave 133 mg (72% of theory) of 1-(3-methoxypyrazin-2-yl)-N-phenylmethylene-4-(3,4,5-trichlorophenyl)-3-(trifluoromethyl)-1H-pyrazol-5-amine as a colourless solid.

LC-MS**: MH+=526.0; 528.0; lgP=6.03

$^1$H-NMR (400 MHz, $d_6$-DMSO), δ 8.56 (s, 1H), 8.54 (d, 1H), 8.35 (d, 1H), 7,77(s, 2H), 7.65-7.44 (m, 5H), 3.90 (s, 3H).

The compounds of the general formulae (IA) and (IB) listed in the tables below are obtained analogously to the preparation examples given above, taking into account the general statements on the preparation of compounds of the formula (I).

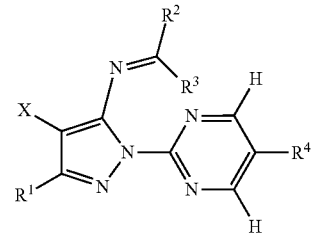

(IA)

TABLE 1

| Ex. No. | $R^1$ | $R^2$ | $R^3$ | $R^4$ | X |
|---|---|---|---|---|---|
| 1-1 | $CF_3$ | H | Dimethylamino | H | 4-Chlorophenyl |
| 1-2 | $CF_3$ | H | Dimethylamino | H | 3-Chloro-5-(trifluoromethyl)phenyl |
| 1-3 | $CF_3$ | H | Dimethylamino | H | 3,4-Dichlorophenyl |
| 1-4 | $CF_2Cl$ | H | Dimethylamino | H | 4-Chlorophenyl |
| 1-5 | $CF_3$ | H | Dimethylamino | H | 4-Methoxyphenyl |
| 1-6 | $CF_3$ | H | Dimethylamino | $CH_3$ | 3,4-Dichlorophenyl |
| 1-7 | $CH_3$ | H | Dimethylamino | H | 4-Chlorophenyl |
| 1-8 | $CF_3$ | H | Dimethylamino | H | 3-Chlorophenyl |
| 1-9 | $CF_3$ | H | Dimethylamino | H | 3-Bromo-5-chlorophenyl |
| 1-10 | $CF_3$ | H | 4-Hydroxy-3-methoxyphenyl | H | 3-Chloro-5-(trifluoromethyl)phenyl |
| 1-11 | $CF_3$ | H | Ethoxy | H | 3-Chloro-5-(trifluoromethyl)phenyl |
| 1-12 | $CF_3$ | H | Phenyl | H | 3-Chloro-5-(trifluoromethyl)phenyl |
| 1-13 | $CF_3$ | H | Propan-2-yloxy | H | 3-Chloro-5-(trifluoromethyl)phenyl |
| 1-14 | $CF_3$ | $CH_3$ | Ethoxy | H | 3-Chloro-5-(trifluoromethyl)phenyl |
| 1-15 | $CF_3$ | H | Butoxy | H | 3-Chloro-5-(trifluoromethyl)phenyl |
| 1-16 | $CF_3$ | H | 4-Chlorophenyl | H | 3-Chloro-5-(trifluoromethyl)phenyl |
| 1-17 | $CF_3$ | H | 4-Methoxyphenyl | H | 3-Chloro-5-(trifluoromethyl)phenyl |
| 1-18 | $CF_3$ | H | Phenyl | H | 7-Chloro-1,3-benzodioxol-5-yl |
| 1-19 | 1,1,2,2-Tetrafluoroethyl | H | Phenyl | H | 3-Chloro-5-(trifluoromethyl)phenyl |
| 1-20 | 1,1,2,2-Tetrafluoroethyl | H | 4-Chlorophenyl | H | 3-Chloro-5-(trifluoromethyl)phenyl |
| 1-21 | 1,1,2,2-Tetrafluoroethyl | H | 4-Methoxyphenyl | H | 3-Chloro-5-(trifluoromethyl)phenyl |
| 1-22 | 1,1,2,2-Tetrafluoroethyl | H | 4-Chlorophenyl | H | 7-Chloro-1,3-benzodioxol-5-yl |
| 1-23 | 1,1,2,2-Tetrafluoroethyl | H | 4-Methoxyphenyl | H | 7-Chloro-1,3-benzodioxol-5-yl |
| 1-24 | 1,1,2,2-Tetrafluoroethyl | H | Phenyl | H | 7-Chloro-1,3-benzodioxol-5-yl |
| 1-25 | $CF_3$ | H | 4-Chlorophenyl | H | 7-Chloro-1,3-benzodioxol-5-yl |
| 1-26 | $CF_3$ | H | 4-Methoxyphenyl | H | 7-Chloro-1,3-benzodioxol-5-yl |
| 1-27 | $CF_3$ | H | 3,4,5-Trimethoxyphenyl | H | 7-Chloro-1,3-benzodioxol-5-yl |
| 1-28 | $CF_3$ | H | 3,4,5-Trimethoxyphenyl | H | 3-Chloro-5-(trifluoromethyl)phenyl |
| 1-29 | 1,1,2,2-Tetrafluoroethyl | H | 3,4,5-Trimethoxyphenyl | H | 3-Chloro-5-(trifluoromethyl)phenyl |
| 1-30 | 1,1,2,2-Tetrafluoroethyl | H | 3,4,5-Trimethoxyphenyl | H | 7-Chloro-1,3-benzodioxol-5-yl |
| 1-31 | $CF_3$ | H | 2-Bromophenyl | H | 3-Chloro-5-(trifluoromethyl)phenyl |
| 1-32 | $CF_3$ | H | Phenyl | H | 7-Bromo-2,3-dihydro-1-benzofur-5-yl |
| 1-33 | $CF_3$ | H | Ethoxy | H | 7-Chloro-1,3-benzodioxol-5-yl |
| 1-34 | 1,1,2,2-Tetrafluoroethyl | H | Ethoxy | H | 3-Chloro-5-(trifluoromethyl)phenyl |
| 1-35 | 1,1,2,2-Tetrafluoroethyl | H | Ethoxy | H | 7-Chloro-1,3-benzodioxol-5-yl |
| 1-36 | $CF_3$ | H | Propan-2-yloxy | H | 7-Chloro-1,3-benzodioxol-5-yl |
| 1-37 | 1,1,2,2-Tetrafluoroethyl | H | Propan-2-yloxy | H | 3-Chloro-5-(trifluoromethyl)phenyl |
| 1-38 | 1,1,2,2-Tetrafluoroethyl | H | Propan-2-yloxy | H | 7-Chloro-1,3-benzodioxol-5-yl |
| 1-39 | $CF_3$ | H | 3-Bromophenyl | H | 3-Chloro-5-(trifluoromethyl)phenyl |
| 1-40 | $C_2F_5$ | H | 4-Chlorophenyl | H | 3-Chloro-5-(trifluoromethyl)phenyl |
| 1-41 | $C_2F_5$ | H | 4-Methoxyphenyl | H | 3-Chloro-5-(trifluoromethyl)phenyl |
| 1-42 | $C_2F_5$ | H | Phenyl | H | 3-Chloro-5-(trifluoromethyl)phenyl |
| 1-43 | $C_2F_5$ | H | Ethoxy | H | 3-Chloro-5-(trifluoromethyl)phenyl |
| 1-44 | $C_2F_5$ | H | Propan-2-yloxy | H | 3-Chloro-5-(trifluoromethyl)phenyl |
| 1-45 | $C_2F_5$ | H | Dimethylamino | H | 3-Chloro-5-(trifluoromethyl)phenyl |
| 1-46 | $CF_3$ | H | Phenyl | H | 3,5-Dichlorophenyl |
| 1-47 | $CF_3$ | H | 4-Chlorophenyl | H | 3,5-Dichlorophenyl |
| 1-48 | $CF_3$ | H | 4-Methoxyphenyl | H | 3,5-Dichlorophenyl |
| 1-49 | $CF_3$ | H | Dimethylamino | H | 3,5-Dichlorophenyl |
| 1-50 | $CF_3$ | H | Methoxy | H | 3,5-Dichlorophenyl |
| 1-51 | $CF_3$ | H | Ethoxy | H | 3,5-Dichlorophenyl |
| 1-52 | $CF_3$ | H | Propan-2-yloxy | H | 3,5-Dichlorophenyl |
| 1-53 | $CF_2Cl$ | H | Phenyl | H | 3,5-Dichlorophenyl |
| 1-54 | $CF_2Cl$ | H | 4-Chlorophenyl | H | 3,5-Dichlorophenyl |
| 1-55 | $CF_2Cl$ | H | 4-Methoxyphenyl | H | 3,5-Dichlorophenyl |
| 1-56 | $CF_2Cl$ | H | Dimethylamino | H | 3,5-Dichlorophenyl |
| 1-57 | $CF_2Cl$ | H | Methoxy | H | 3,5-Dichlorophenyl |
| 1-58 | $CF_2Cl$ | H | Ethoxy | H | 3,5-Dichlorophenyl |
| 1-59 | $CF_2Cl$ | H | Propan-2-yloxy | H | 3,5-Dichlorophenyl |
| 1-60 | $C_2F_5$ | H | Phenyl | H | 3,5-Dichlorophenyl |

TABLE 1-continued

| Ex. No. | R¹ | R² | R³ | R⁴ | X |
|---|---|---|---|---|---|
| 1-61 | $C_2F_5$ | H | 4-Chlorophenyl | H | 3,5-Dichlorophenyl |
| 1-62 | $C_2F_5$ | H | 4-Methoxyphenyl | H | 3,5-Dichlorophenyl |
| 1-63 | $C_2F_5$ | H | Dimethylamino | H | 3,5-Dichlorophenyl |
| 1-64 | $C_2F_5$ | H | Methoxy | H | 3,5-Dichlorophenyl |
| 1-65 | $C_2F_5$ | H | Ethoxy | H | 3,5-Dichlorophenyl |
| 1-66 | $C_2F_5$ | H | Propan-2-yloxy | H | 3,5-Dichlorophenyl |
| 1-67 | $CF_3$ | H | Phenyl | H | 3-Chloro-4-(trifluoromethyl)phenyl |
| 1-68 | $CF_3$ | H | 4-Chlorophenyl | H | 3-Chloro-4-(trifluoromethyl)phenyl |
| 1-69 | $CF_3$ | H | 4-Methoxyphenyl | H | 3-Chloro-4-(trifluoromethyl)phenyl |
| 1-70 | $CF_3$ | H | Dimethylamino | H | 3-Chloro-4-(trifluoromethyl)phenyl |
| 1-71 | $CF_3$ | H | Methoxy | H | 3-Chloro-4-(trifluoromethyl)phenyl |
| 1-72 | $CF_3$ | H | Ethoxy | H | 3-Chloro-4-(trifluoromethyl)phenyl |
| 1-73 | $CF_3$ | H | Propan-2-yloxy | H | 3-Chloro-4-(trifluoromethyl)phenyl |
| 1-74 | $CF_3$ | H | Phenyl | H | 3,4-Dichlorophenyl |
| 1-75 | $CF_3$ | H | 4-Chlorophenyl | H | 3,4-Dichlorophenyl |
| 1-76 | $CF_3$ | H | 4-Methoxyphenyl | H | 3,4-Dichlorophenyl |
| 1-77 | $CF_3$ | H | Methoxy | H | 3,4-Dichlorophenyl |
| 1-78 | $CF_3$ | H | Ethoxy | H | 3,4-Dichlorophenyl |
| 1-79 | $CF_3$ | H | Propan-2-yloxy | H | 3,4-Dichlorophenyl |
| 1-80 | $CF_2Cl$ | H | Phenyl | H | 3-Chloro-5-(trifluoromethyl)phenyl |
| 1-81 | $CF_2Cl$ | H | 4-Chlorophenyl | H | 3-Chloro-5-(trifluoromethyl)phenyl |
| 1-82 | $CF_2Cl$ | H | 4-Methoxyphenyl | H | 3-Chloro-5-(trifluoromethyl)phenyl |
| 1-83 | $CF_2Cl$ | H | Dimethylamino | H | 3-Chloro-5-(trifluoromethyl)phenyl |
| 1-84 | $CF_2Cl$ | H | Methoxy | H | 3-Chloro-5-(trifluoromethyl)phenyl |
| 1-85 | $CF_2Cl$ | H | Ethoxy | H | 3-Chloro-5-(trifluoromethyl)phenyl |
| 1-86 | $CF_2Cl$ | H | Propan-2-yloxy | H | 3-Chloro-5-(trifluoromethyl)phenyl |
| 1-87 | $CF_3$ | H | Phenyl | H | 4-Chloro-3-(trifluoromethyl)phenyl |
| 1-88 | $CF_3$ | H | 4-Chlorophenyl | H | 4-Chloro-3-(trifluoromethyl)phenyl |
| 1-89 | $CF_3$ | H | 4-Methoxyphenyl | H | 4-Chloro-3-(trifluoromethyl)phenyl |
| 1-90 | $CF_3$ | H | Dimethylamino | H | 4-Chloro-3-(trifluoromethyl)phenyl |
| 1-91 | $CF_3$ | H | Methoxy | H | 4-Chloro-3-(trifluoromethyl)phenyl |
| 1-92 | $CF_3$ | H | Ethoxy | H | 4-Chloro-3-(trifluoromethyl)phenyl |
| 1-93 | $CF_3$ | H | Propan-2-yloxy | H | 4-Chloro-3-(trifluoromethyl)phenyl |
| 1-94 | $CF_3$ | H | Phenyl | H | 4-Bromophenyl |
| 1-95 | $CF_3$ | H | 4-Chlorophenyl | H | 4-Bromophenyl |
| 1-96 | $CF_3$ | H | 4-Methoxyphenyl | H | 4-Bromophenyl |
| 1-97 | $CF_3$ | H | Dimethylamino | H | 4-Bromophenyl |
| 1-98 | $CF_3$ | H | Methoxy | H | 4-Bromophenyl |
| 1-99 | $CF_3$ | H | Ethoxy | H | 4-Bromophenyl |
| 1-100 | $CF_3$ | H | Propan-2-yloxy | H | 4-Bromophenyl |
| 1-101 | $CF_3$ | H | Phenyl | H | 3,4,5-Trichlorophenyl |
| 1-102 | $CF_3$ | H | 4-Chlorophenyl | H | 3,4,5-Trichlorophenyl |
| 1-103 | $CF_3$ | H | 4-Methoxyphenyl | H | 3,4,5-Trichlorophenyl |
| 1-104 | $CF_3$ | H | Dimethylamino | H | 3,4,5-Trichlorophenyl |
| 1-105 | $CF_3$ | H | Methoxy | H | 3,4,5-Trichlorophenyl |
| 1-106 | $CF_3$ | H | Ethoxy | H | 3,4,5-Trichlorophenyl |
| 1-107 | $CF_3$ | H | Propan-2-yloxy | H | 3,4,5-Trichlorophenyl |
| 1-108 | $CF_3$ | H | Dimethylamino | Cl | 4-Chlorophenyl |

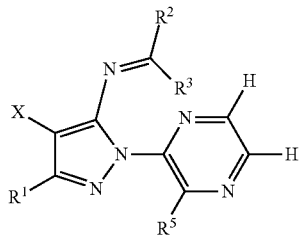

TABLE 2

| Ex. No. | R¹ | R² | R³ | R⁵ | X |
|---|---|---|---|---|---|
| 2-1 | $CF_3$ | H | Dimethylamino | Methoxy | 3-Chloro-5-(trifluoromethyl)phenyl |
| 2-2 | $CF_3$ | H | Dimethylamino | Ethoxy | 3-Chloro-5-(trifluoromethyl)phenyl |
| 2-3 | $CF_3$ | H | Dimethylamino | Propan-2-yloxy | 3-Chloro-5-(trifluoromethyl)phenyl |
| 2-4 | $CF_3$ | H | Dimethylamino | H | 3-Chloro-5-(trifluoromethyl)phenyl |
| 2-5 | $CF_3$ | H | 4-Methoxyphenyl | Methoxy | 7-Chloro-1,3-benzodioxol-5-yl |
| 2-6 | $CF_3$ | H | Phenyl | Methoxy | 7-Chloro-1,3-benzodioxol-5-yl |
| 2-7 | $CF_3$ | H | 4-Chlorophenyl | Methoxy | 3-Chloro-5-(trifluoromethyl)phenyl |

TABLE 2-continued

| Ex. No. | R$^1$ | R$^2$ | R$^3$ | R$^5$ | X |
|---|---|---|---|---|---|
| 2-8 | CF$_3$ | H | 4-Methoxyphenyl | Methoxy | 3-Chloro-5-(trifluoromethyl)phenyl |
| 2-9 | CF$_3$ | H | Phenyl | Methoxy | 3-Chloro-5-(trifluoromethyl)phenyl |
| 2-10 | 1,1,2,2-Tetrafluoroethyl | H | 4-Methoxyphenyl | Methoxy | 3-Chloro-5-(trifluoromethyl)phenyl |
| 2-11 | 1,1,2,2-Tetrafluoroethyl | H | Phenyl | Methoxy | 3-Chloro-5-(trifluoromethyl)phenyl |
| 2-12 | 1,1,2,2-Tetrafluoroethyl | H | 4-Methoxyphenyl | Methoxy | 7-Chloro-1,3-benzodioxol-5-yl |
| 2-13 | 1,1,2,2-Tetrafluoroethyl | H | Phenyl | Methoxy | 7-Chloro-1,3-benzodioxol-5-yl |
| 2-14 | CF$_3$ | H | 4-Chlorophenyl | Methoxy | 7-Chloro-1,3-benzodioxol-5-yl |
| 2-15 | CF$_3$ | H | Phenyl | Methoxy | 3,4,5-Trichlorophenyl |
| 2-16 | CF$_3$ | H | 3,4,5-Trimethoxyphenyl | Methoxy | 3-Chloro-5-(trifluoromethyl)phenyl |
| 2-17 | 1,1,2,2-Tetrafluoroethyl | H | 3,4,5-Trimethoxyphenyl | Methoxy | 3-Chloro-5-(trifluoromethyl)phenyl |
| 2-18 | CF$_3$ | H | Ethoxy | Methoxy | 7-Chloro-1,3-benzodioxol-5-yl |
| 2-19 | CF$_3$ | H | Propan-2-yloxy | Methoxy | 7-Chloro-1,3-benzodioxol-5-yl |
| 2-20 | 1,1,2,2-Tetrafluoroethyl | H | Propan-2-yloxy | Methoxy | 3-Chloro-5-(trifluoromethyl)phenyl |
| 2-21 | CF$_3$ | H | Phenyl | Methoxy | 3,5-Dichlorophenyl |
| 2-22 | CF$_3$ | H | 4-Chlorophenyl | Methoxy | 3,5-Dichlorophenyl |
| 2-23 | CF$_3$ | H | 4-Methoxyphenyl | Methoxy | 3,5-Dichlorophenyl |
| 2-24 | CF$_3$ | H | Dimethylamino | Methoxy | 3,5-Dichlorophenyl |
| 2-25 | CF$_3$ | H | Methoxy | Methoxy | 3,5-Dichlorophenyl |
| 2-26 | CF$_3$ | H | Ethoxy | Methoxy | 3,5-Dichlorophenyl |
| 2-27 | CF$_3$ | H | Propan-2-yloxy | Methoxy | 3,5-Dichlorophenyl |
| 2-28 | CF$_2$Cl | H | Phenyl | Methoxy | 3,5-Dichlorophenyl |
| 2-29 | CF$_2$Cl | H | 4-Chlorophenyl | Methoxy | 3,5-Dichlorophenyl |
| 2-30 | CF$_2$Cl | H | 4-Methoxyphenyl | Methoxy | 3,5-Dichlorophenyl |
| 2-31 | CF$_2$Cl | H | Dimethylamino | Methoxy | 3,5-Dichlorophenyl |
| 2-32 | CF$_2$Cl | H | Methoxy | Methoxy | 3,5-Dichlorophenyl |
| 2-33 | CF$_2$Cl | H | Ethoxy | Methoxy | 3,5-Dichlorophenyl |
| 2-34 | CF$_2$Cl | H | Propan-2-yloxy | Methoxy | 3,5-Dichlorophenyl |
| 2-35 | C$_2$F$_5$ | H | Phenyl | Methoxy | 3,5-Dichlorophenyl |
| 2-36 | C$_2$F$_5$ | H | 4-Chlorophenyl | Methoxy | 3,5-Dichlorophenyl |
| 2-37 | C$_2$F$_5$ | H | 4-Methoxyphenyl | Methoxy | 3,5-Dichlorophenyl |
| 2-38 | C$_2$F$_5$ | H | Dimethylamino | Methoxy | 3,5-Dichlorophenyl |
| 2-39 | C$_2$F$_5$ | H | Methoxy | Methoxy | 3,5-Dichlorophenyl |
| 2-40 | C$_2$F$_5$ | H | Ethoxy | Methoxy | 3,5-Dichlorophenyl |
| 2-41 | C$_2$F$_5$ | H | Propan-2-yloxy | Methoxy | 3,5-Dichlorophenyl |
| 2-42 | CF$_3$ | H | Phenyl | Methoxy | 3-Chloro-4-(trifluoromethyl)phenyl |
| 2-43 | CF$_3$ | H | 4-Chlorophenyl | Methoxy | 3-Chloro-4-(trifluoromethyl)phenyl |
| 2-44 | CF$_3$ | H | 4-Methoxyphenyl | Methoxy | 3-Chloro-4-(trifluoromethyl)phenyl |
| 2-45 | CF$_3$ | H | Dimethylamino | Methoxy | 3-Chloro-4-(trifluoromethyl)phenyl |
| 2-46 | CF$_3$ | H | Methoxy | Methoxy | 3-Chloro-4-(trifluoromethyl)phenyl |
| 2-47 | CF$_3$ | H | Ethoxy | Methoxy | 3-Chloro-4-(trifluoromethyl)phenyl |
| 2-48 | CF$_3$ | H | Propan-2-yloxy | Methoxy | 3-Chloro-4-(trifluoromethyl)phenyl |
| 2-49 | CF$_3$ | H | Phenyl | Methoxy | 3,4-Dichlorophenyl |
| 2-50 | CF$_3$ | H | 4-Chlorophenyl | Methoxy | 3,4-Dichlorophenyl |
| 2-51 | CF$_3$ | H | 4-Methoxyphenyl | Methoxy | 3,4-Dichlorophenyl |
| 2-52 | CF$_3$ | H | Dimethylamino | Methoxy | 3,4-Dichlorophenyl |
| 2-53 | CF$_3$ | H | Methoxy | Methoxy | 3,4-Dichlorophenyl |
| 2-54 | CF$_3$ | H | Ethoxy | Methoxy | 3,4-Dichlorophenyl |
| 2-55 | CF$_3$ | H | Propan-2-yloxy | Methoxy | 3,4-Dichlorophenyl |
| 2-56 | CF$_2$Cl | H | Phenyl | Methoxy | 3-Chloro-5-(trifluoromethyl)phenyl |
| 2-57 | CF$_2$Cl | H | 4-Chlorophenyl | Methoxy | 3-Chloro-5-(trifluoromethyl)phenyl |
| 2-58 | CF$_2$Cl | H | 4-Methoxyphenyl | Methoxy | 3-Chloro-5-(trifluoromethyl)phenyl |
| 2-59 | CF$_2$Cl | H | Dimethylamino | Methoxy | 3-Chloro-5-(trifluoromethyl)phenyl |
| 2-60 | CF$_2$Cl | H | Methoxy | Methoxy | 3-Chloro-5-(trifluoromethyl)phenyl |
| 2-61 | CF$_2$Cl | H | Ethoxy | Methoxy | 3-Chloro-5-(trifluoromethyl)phenyl |
| 2-62 | CF$_2$Cl | H | Propan-2-yloxy | Methoxy | 3-Chloro-5-(trifluoromethyl)phenyl |
| 2-63 | CF$_3$ | H | Phenyl | Methoxy | 4-Chloro-3-(trifluoromethyl)phenyl |
| 2-64 | CF$_3$ | H | 4-Chlorophenyl | Methoxy | 4-Chloro-3-(trifluoromethyl)phenyl |
| 2-65 | CF$_3$ | H | 4-Methoxyphenyl | Methoxy | 4-Chloro-3-(trifluoromethyl)phenyl |
| 2-66 | CF$_3$ | H | Dimethylamino | Methoxy | 4-Chloro-3-(trifluoromethyl)phenyl |
| 2-67 | CF$_3$ | H | Methoxy | Methoxy | 4-Chloro-3-(trifluoromethyl)phenyl |
| 2-68 | CF$_3$ | H | Ethoxy | Methoxy | 4-Chloro-3-(trifluoromethyl)phenyl |
| 2-69 | CF$_3$ | H | Propan-2-yloxy | Methoxy | 4-Chloro-3-(trifluoromethyl)phenyl |
| 2-70 | CF$_3$ | H | Phenyl | Methoxy | 4-Bromophenyl |
| 2-71 | CF$_3$ | H | 4-Chlorophenyl | Methoxy | 4-Bromophenyl |
| 2-72 | CF$_3$ | H | 4-Methoxyphenyl | Methoxy | 4-Bromophenyl |
| 2-73 | CF$_3$ | H | Dimethylamino | Methoxy | 4-Bromophenyl |
| 2-74 | CF$_3$ | H | Methoxy | Methoxy | 4-Bromophenyl |
| 2-75 | CF$_3$ | H | Ethoxy | Methoxy | 4-Bromophenyl |
| 2-76 | CF$_3$ | H | Propan-2-yloxy | Methoxy | 4-Bromophenyl |
| 2-77 | CF$_3$ | H | 4-Chlorophenyl | Methoxy | 3,4,5-Trichlorophenyl |
| 2-78 | CF$_3$ | H | 4-Methoxyphenyl | Methoxy | 3,4,5-Trichlorophenyl |
| 2-79 | CF$_3$ | H | Dimethylamino | Methoxy | 3,4,5-Trichlorophenyl |
| 2-80 | CF$_3$ | H | Methoxy | Methoxy | 3,4,5-Trichlorophenyl |
| 2-81 | CF$_3$ | H | Ethoxy | Methoxy | 3,4,5-Trichlorophenyl |
| 2-82 | CF$_3$ | H | Propan-2-yloxy | Methoxy | 3,4,5-Trichlorophenyl |

TABLE 3

Analytical data

| Ex. | ¹H-NMR (400 MHz) | MH+ | logp |
|---|---|---|---|
| 1-1 | d₆-DMSO, δ 8.95 (d, 2H), 7.60 (t, 1H), 7.56 (s, 1H), 7.48 (d, 2H), 7.30 (d, 2H), 2.80 (br s, 3H), 2.75 (br s, 3H) | 395.1 | 2.68* |
| 1-2 | d₆-DMSO, δ 8.95 (d, 2H), 7.75 (m, 2H), 7.71 (s, 1H), 7.64 (s, 1H), 7.61 (t, 1H), 2.84 (s, 3H), 2.80 (s, 3H) | 463 | 3.84**; 3.89* |
| 1-3 | d₆-DMSO, δ 8.93 (d, 2H), 7.64 (d, 1H), 7.62-7.59 (m, 3H), 7.35 (dd, 1H), 2.84 (s, 3H), 2.78 (s, 3H) | 429 | 3.37* |
| 1-4 | d₆-DMSO, δ 8.97 (d, 2H), 7.63 (t, 1H), 7.59 (s, 1H), 7.48 (d, 2H), 7.41 (d, 2H), 2.81 (s, 3H), 2.73 (s, 3H) | 411 | 2.8* |
| 1-5 | d₆-DMSO, δ 8.96 (d, 2H), 7.63 (t, 1H), 7.60 (s, 1H), 7.29 (d, 2H), 6.98 (d, 2H), 3.79 (s, 3H), 2.80 (s, 3H), 2.73 (s, 3H) | 391 | 1.87* |
| 1-6 | d₆-DMSO, δ 8.80 (s, 2H), 7.70-7.63 (m, 3H), 7.36 (d, 1H), 2.85 (s, 3H), 2.76 (s, 3H), 2.37 (s, 3H) | 443 | 3.58* |
| 1-7 | d₆-DMSO, δ 8.84 (d, 2H), 7.51-7.41 (m, 6H), 2.85 (s, 3H), 2.83 (s, 3H), 2.23 (s, 3H) | 341 | 1.09* |
| 1-8 | d₆-DMSO, δ 8.97 (d, 2H), 7.65 (t, 1H), 7.62 (s, 1H), 7.48-7.34 (m, 4H), 2.83 (s, 3H), 2.77 (s, 3H) | 395 | 2.65* |
| 1-9 | d₆-DMSO, δ 8.94 (d, 2H), 7.64-7.61 (m, 3H), 7.55 (s, 1H), 7.45 (s, 1H), 2.86 (br s, 3H), 2.78 (br s, 3H) | 473.0; 474.9 | 3.71* |
| 1-10 | d₆-DMSO, δ 8.97 (d, 2H), 8.40 (s, 1H), 7.90 (s, 1H), 7.85 (s, 1H), 7.80 (s, 1H), 7.67 (m, 3H), 7.30 (d, 1H), 7.13 (dd, 1H), 6.84 (d, 1H), 3.74 (s, 3H) | 542 | 4.05** |
| 1-11 | d₆-DMSO, δ 8.96 (d, 2H), 8.11 (br. s, 1H), 7.85 (s, 1H), 7.75 (s, 1H), 7.68 (s, 1H), 7.65 (t, 1H), 4.17 (br. s, 2H), 1.15 (br. s, 3H) | 464 | 4.58**; 4.61* |
| 1-12 | d₆-DMSO, δ 8.98 (d, 2H), 8.62 (s, 1H), 7.92 (s, 1H), 7.87 (s, 1H), 7.81 (s, 1H), 7.69 (m, 3H), 7.59 (m, 1H), 7.49 (m, 2H) | 496 | 4.92** |
| 1-13 | CD₃CN: δ 8.85 (d, 2H), 7.73 (br. s, 1H), 7.75 (s, 1H), 7.68 (s, 1H), 7.64 (s, 1H), 7.48 (t, 1H), 5.03 (br. s, 1H), 1.20 (br. s, 6H) | 478 | 4.75** |
| 1-14 | CD₃CN: δ 8.83 (d, 2H), 7.68 (s, 1H), 7.66 (s, 1H), 7.63 (s, 1H), 7.45 (t, 1H), 4.19 (q, 2H), 1.76 (s, 3H), 1.20 (t, 3H) | 478 | 5.01** |
| 1-15 | CD₃CN: δ 8.85 (d, 2H), 7.75 (br. s, 1H), 7.71 (s, 1H), 7.68 (s, 1H), 7.64 (s, 1H), 7.48 (t, 1H), 4.16 (br. s, 2H), 1.58 (br. s, 2H), 1.28 (br. s, 2H), 1.12 (br. s, 3H) | 492 | 5.24** |
| 1-16 | d₆-DMSO, δ 8.97 (d, 2H), 8.62 (s, 1H), 7.92 (s, 1H), 7.85 (s, 1H), 7.78 (s, 1H), 7.74 (d, 2H), 7.68 (t, 1H), 7.57 (d, 2H) | 530 | 5.53** |
| 1-17 | d₆-DMSO, δ 8.97 (d, 2H), 8.49 (s, 1H), 7.90 (s, 1H), 7.84 (s, 1H), 7.78 (s, 1H), 7.67 (m, 3H), 7.03 (d, 2H), 3.82 (s, 3H) | 526 | 4.98** |
| 1-18 | d₆-DMSO, δ 8.96 (d, 2H), 8.61 (s, 1H), 7.72 (m, 2H), 7.66 (t, 1H), 7.58 (m, 1H), 7.49 (m, 2H), 7.01 (d, 1H), 6.99 (d, 1H), 6.18 (s, 2H) | 472 | 3.97** |
| 1-19 | d₆-DMSO, δ 8.97 (d, 2H), 8.61 (s, 1H), 7.88 (s, 1H), 7.84 (s, 1H), 7.78 (s, 1H), 7.69 (m, 3H), 7.58 (m, 1H), 7.48 (m, 2H), 6.96 (tt, 1H) | 528 | 4.86** |
| 1-20 | d₆-DMSO, δ 8.97 (d, 2H), 8.61 (s, 1H), 7.89 (s, 1H), 7.83 (s, 1H), 7.75 (s, 1H), 7.71 (d, 2H), 7.67 (t, 1H), 7.56 (d, 2H), 6.95 (tt, 1H) | 562 | 5.37** |
| 1-21 | d₆-DMSO, δ 8.96 (d, 2H), 8.48 (s, 1H), 7.87 (s, 1H), 7.82 (s, 1H), 7.76 (s, 1H), 7.66 (m, 3H), 7.02 (d, 2H), 6.95 (tt, 1H), 3.81 (s, 3H) | 558 | 3.69** |
| 1-22 | d₆-DMSO, δ 8.96 (d, 2H), 8.59 (s, 1H), 7.73 (d, 2H), 7.66 (t, 1H), 7.55 (d, 2H), 6.98 (d, 1H), 6.95 (d, 1H), 6.88 (tt, 1H), 6.17 (s, 2H) | 538 | 4.34** |
| 1-23 | d₆-DMSO, δ 8.95 (d, 2H), 8.47 (s, 1H), 7.67 (m, 3H), 7.02 (d, 2H), 6.97 (d, 1H), 6.94 (d, 1H), 6.87 (tt, 1H), 6.17 (s, 2H), 3.81 (s, 3H) | 534 | 3.85** |
| 1-24 | d₆-DMSO, δ 8.96 (d, 2H), 8.59 (s, 1H), 7.71 (m, 2H), 7.66 (t, 1H), 7.57 (m, 1H), 7.48 (m, 2H), 6.99 (d, 1H), 6.96 (d, 1H), 6.88 (tt, 1H), 6.17 (s, 2H) | 504 | 3.9** |
| 1-25 | d₆-DMSO, δ 8.96 (d, 2H), 8.609 (s, 1H), 7.76 (d, 2H), 7.67 (t, 1H), 7.56 (d, 2H), 7.00 (d, 1H), 6.98 (d, 1H), 6.18 (s, 2H) | 506 | 4.51** |
| 1-26 | d₆-DMSO, δ 8.96 (d, 2H), 8.49 (s, 1H), 7.68 (m, 3H), 7.02 (d, 2H), 6.98 (d, 1H), 6.96 (d, 1H), 6.17 (s, 2H), 3.82 (s, 3H) | 502 | 3.97** |
| 1-27 | d₆-DMSO, δ 8.97 (d, 2H), 8.50 (s, 1H), 7.65 (t, 1H), 7.09 (s, 2H), 7.01 (d, 1H), 6.97 (d, 1H), 6.18 (s, 2H), 3.77 (s, 6H), 3.73 (s, 3H) | 562 | 3.82** |
| 1-28 | d₆-DMSO, δ 8.98 (d, 2H), 8.51 (s, 1H), 7.91 (s, 1H), 7.87 (s, 1H), 7.81 (s, 1H), 7.67 (t, 1H), 7.08 (s, 2H), 3.76 (s, 6H), 3.73 (s, 3H) | 586 | 4.85** |
| 1-29 | d₆-DMSO, δ 8.97 (d, 2H), 8.51 (s, 1H), 7.89 (s, 1H), 7.85 (s, 1H), 7.80 (s, 1H), 7.67 (t, 1H), 7.06 (s, 2H), 6.98 (tt, 1H), 3.75 (s, 6H), 3.72 (s, 3H) | 618 | 4.67** |
| 1-30 | d₆-DMSO, δ 8.96 (d, 2H), 8.48 (s, 1H), 7.65 (t, 1H), 7.07 (s, 2H), 6.99 (d, 1H), 6.91 (d, 1H), 6.88 (tt, 1H), 6.17 (s, 2H), 3.76 (s, 6H), 3.72 (s, 3H) | 594 | 3.72** |
| 1-31 | d₆-DMSO, δ 9.04 (d, 2H), 8.74 (s, 1H), 7.96 (s, 2H), 7.88 (m, 2H), 7.71 (m, 2H), 7.49 (m, 2H) | 576 | 5.64** |
| 1-32 | CD₃CN: δ 8.85 (d, 2H), 8.43 (s, 1H), 7.69-7.42 (m, 6H), 7.34 (s, 1H), 7.25 (s, 1H), 4.65 (t, 2H), 3.3 (t, 2H) | 514.0, 516 | 4.11** |
| 1-33 | d₆-DMSO, δ 8.98 (d, 2H), 8.16 (s, 1H), 7.66 (t, 1H), 6.94 (s, 1H), 6.92 (s, 1H), 6.20 (s, 2H), 4.14 (q, 2H), 1.18 (t, 3H) | 440 | 3.49** |
| 1-34 | d₆-DMSO, δ 8.99 (d, 2H), 8.19 (s, 1H), 7.89 (s, 1H), 7.77 (s, 1H), 7.70 (s, 1H), 7.67 (t, 1H), 6.93 (tt, 1H), 4.15 (q, 2H), 1.17 (t, 3H) | 496 | 4.43** |
| 1-35 | d₆-DMSO, δ 8.98 (d, 2H), 8.14 (s, 1H), 7.65 (t, 1H), 6.92 (s, 1H), 6.90 (s, 1H), 6.84 (tt, 1H), 6.19 (s, 2H), 4.13 (q, 2H), 1.17 (t, 3H) | 472 | 3.42** |
| 1-36 | d₆-DMSO, δ 8.97 (d, 2H), 8.09 (s, 1H), 7.66 (t, 1H), 6.93 (s, 1H), 6.91 (s, 1H), 6.20 (s, 2H), 4.92 (m, 1H), 1.18 (d, 6H) | 545 | 3.72** |
| 1-38 | d₆-DMSO, δ 8.97 (d, 2H), 8.08 (s, 1H), 7.65 (t, 1H), 6.91 (s, 1H), 6.90 (s, 1H), 6.85 (tt, 1H), 6.19 (s, 2H), 4.90 (m, 1H), 1.17 (d, 6H) | 486 | 3.66** |
| 1-39 | d₆-DMSO, δ 8.97 (d, 2H), 8.60 (s, 1H), 7.92 (s, 1H), 7.90 (s, 1H), 7.85 (s, 1H), 7.78 (m, 2H), 7.72 (d, 1H), 7.68 (t, 1H), 7.46 (t, 1H) | | |
| 1-40 | d₆-DMSO, δ 8.98 (d, 2H), 8.61 (s, 1H), 7.92 (s, 1H), 7.82 (s, 1H), 7.80 (s, 1H), 7.69 (m, 3H), 7.55 (d, 2H) | 580 | 5.93** |
| 1-41 | d₆-DMSO, δ 8.98 (d, 2H), 8.50 (s, 1H), 7.90 (s, 1H), 7.86 (s, 1H), 7.79 (s, 1H), 7.68 (t, 1H), 7.63 (d, 2H), 7.02 (d, 2H), 3.81 (s, 3H) | 576 | 5.4** |
| 1-42 | d₆-DMSO, δ 8.99 (d, 2H), 8.62 (s, 1H), 7.91 (s, 1H), 7.88 (s, 1H), 7.82 (s, 1H), 7.69 (m, 3H), 7.58 (m, 1H), 7.48 (m, 2H) | 546 | 5.46** |
| 1-43 | d₆-DMSO, δ 9.00 (d, 2H), 8.20 (s, 1H), 7.92 (s, 1H), 7.80 (s, 1H), 7.72 (s, 1H), 7.69 (t, 1H), 4.13 (q, 2H), 1.15 (t, 3H) | 514 | 5.02** |
| 1-44 | d₆-DMSO, δ 9.00 (d, 2H), 8.13 (s, 1H), 7.92 (s, 1H), 7.79 (s, 1H), 7.71 (s, 1H), 7.69 (t, 1H), 4.91 (m, 1H), 1.15 (d, 6H) | 528 | 5.31** |
| 1-108 | d₆-DMSO, δ 9.09 (s, 2H), 7.61 (s, 1H), 7.49 (d, 2H), 7.39 (d, 2H), 2.84 (s, 3H), 2.78 (s, 3H) | 429 | 3.47* |
| 2-1 | d₆-DMSO, δ 8.45 (d, 1H), 8.28 (d, 1H), 7.77 (s, 1H), 7.72 (s, 1H), 7.67 (s, 1H), 7.56 (s, 1H), 3.95 (s, 3H), 2.79 (s, 3H), 2.69 (s, 3H) | 493 | 4.52* |
| 2-2 | d₆-DMSO, δ 8.42 (d, 1H), 8.26 (d, 1H), 7.77 (s, 1H), 7.72 (s, 1H), 7.66 (s, 1H), 7.55 (s, 1H), 4.43 (q, 2H), 2.79 (s, 3H), 2.70 (s, 3H), 1.27 (t, 3H) | 507 | 4.86* |
| 2-3 | d₆-DMSO, δ 8.40 (d, 1H), 8.23 (d, 1H), 7.77 (s, 1H), 7.71 (s, 1H), 7.64 (s, 1H), 7.53 (s, 1H), 5.31 (m, 1H), 2.79 (s, 3H), 2.70 (s, 3H), 1.26 (d, 6H) | 521 | 5.17* |
| 2-4 | d₆-DMSO, δ 9.06 (d, 1H), 8.71 (d, 1H), 8.65 (m, 1H), 7.79 (s, 1H), 7.73 (s, 1H), 7.68 (s, 1H), 7.63 (s, 1H), 2.84 (s, 3H), 2.83 (s, 3H) | 463 | 4.32* |

TABLE 3-continued

Analytical data

| Ex. | ¹H-NMR (400 MHz) | MH+ | logp |
|---|---|---|---|
| 2-5 | d₆-DMSO, δ 8.51 (d, 1H), 8.43 (s, 1H), 8.32 (d, 1H), 7.58 (d, 2H), 6.99 (m, 4H), 6.19 (s, 2H), 3.89 (s, 3H), 3.80 (s, 3H) | 532 | 4.5** |
| 2-6 | d₆-DMSO, δ 8.53 (m, 2H), 8.33 (d, 1H), 7.58 (m, 3H), 7.45 (m, 2H), 7.02 (d, 1H), 7.01 (d, 1H), 6.19 (s, 2H), 3.90 (s, 3H) | 502 | 4.58** |
| 2-7 | d₆-DMSO, δ 8.54 (d, 2H), 8.34 (d, 1H), 7.94 (s, 1H), 7.87 (s, 1H), 7.79 (s, 1H), 7.62 (d, 2H), 7.53 (d, 2H), 3.90 (s, 3H) | 560 | 6.01** |
| 2-8 | d₆-DMSO, δ 8.53 (d, 1H), 8.42 (s, 1H), 8.34 (d, 1H), 7.92 (s, 1H), 7.85 (s, 1H), 7.80 (s, 1H), 7.57 (d, 2H), 6.99 (d, 2H), 3.90 (s, 3H), 3.80 (s, 3H) | 556 | 5.48** |
| 2-9 | d₆-DMSO, δ 8.54 (d, 2H), 8.35 (d, 1H), 7.93 (s, 1H), 7.88 (s, 1H), 7.81 (s, 1H), 7.58 (m, 3H), 7.45 (m, 2H), 3.91 (s, 3H) | 526 | 5.56** |
| 2-10 | d₆-DMSO, δ 8.52 (d, 1H), 8.41 (s, 1H), 8.34 (d, 1H), 7.89 (s, 1H), 7.83 (s, 1H), 7.75 (s, 1H), 7.56 (d, 2H), 6.99 (d, 2H), 6.92 (tt, 1H), 3.88 (s, 3H), 3.79 (s, 3H) | 588 | 5.29** |
| 2-11 | d₆-DMSO, δ 8.53 (m, 2H), 8.35 (d, 1H), 7.91 (s, 1H), 7.85 (s, 1H), 7.79 (s, 1H), 7.57 (m, 3H), 6.95 (m, 2H), 6.93 (tt, 1H), 3.89 (s, 3H) | 558 | 5.37** |
| 2-12 | d₆-DMSO, δ 8.50 (d, 1H), 8.41 (s, 1H), 8.32 (d, 1H), 7.58 (d, 2H), 6.97 (m, 4H), 6.85 (tt, 1H), 6.18 (s, 2H), 3.88 (s, 3H), 3.79 (s, 3H) | 564 | 4.41** |
| 2-13 | d₆-DMSO, δ 8.52 (m, 2H), 8.33 (d, 1H), 7.58 (m, 3H), 7.45 (m, 2H), 7.00 (d, 1H), 6.97 (d, 1H), 6.85 (tt, 1H), 6.19 (s, 2H), 3.88 (s, 3H) | 534 | 4.48** |
| 2-14 | d₆-DMSO, δ 8.53 (d, 2H), 8.33 (d, 1H), 7.63 (d, 2H), 7.52 (d, 2H), 7.01 (d, 1H), 6.99 (d, 1H), 6.19 (s, 2H), 3.90 (s, 3H) | 536 | 5.1** |
| 2-15 | d₆-DMSO, δ 8.56 (s, 1H), 8.54 (d, 1H), 8.35 (d, 1H), 7.77 (s, 2H), 7.65-7.44 (m, 5H), 3.90 (s, 3H) | 526.0; 528.0 | 6.03** |
| 2-16 | d₆-DMSO, δ 8.53 (d, 1H), 8.43 (s, 1H), 8.35 (d, 1H), 7.91 (s, 1H), 7.85 (s, 1H), 7.79 (s, 1H), 6.95 (s, 2H), 6.94 (tt, 1H), 3.92 (s, 3H), 3.72 (s, 6H), 3.71 (s, 3H) | 616 | 5.35** |
| 2-17 | d₆-DMSO, δ 8.53 (d, 1H), 8.43 (s, 1H), 8.35 (d, 1H), 7.91 (s, 1H), 7.85 (s, 1H), 7.79 (s, 1H), 6.95 (s, 2H), 6.94 (tt, 1H), 3.92 (s, 3H), 3.72 (s, 6H), 3.71 (s, 3H | 648 | 5.12** |
| 2-18 | d₆-DMSO, δ 8.51 (d, 1H), 8.32 (d, 1H), 8.09 (s, 1H), 6.94 (d, 1H), 6.93 (d, 1H), 6.20 (s, 2H), 4.01 (q, 2H), 3.96 (s, 3H), 1.06 (t, 3H) | 470 | 4.03** |
| 2-19 | d₆-DMSO, δ 8.51 (d, 1H), 8.32 (d, 1H), 8.03 (s, 1H), 6.93 (m, 2H), 6.20 (s, 2H), 4.76 (m, 1H), 3.96 (s, 3H), 1.06 (d, 6H) | 484 | 4.26** |
| 2-20 | d₆-DMSO, δ 8.53 (d, 1H), 8.34 (d, 1H), 8.04 (s, 1H), 7.90 (s, 1H), 7.77 (s, 1H), 7.68 (s, 1H), 6.89 (tt, 1H), 4.78 (m, 1H), 3.96 (s, 3H), 1.06 (d, 6H) | 540 | 5.1** |

The logP values were determined in accordance with EU Guideline 79/831 Annex V.A8 by HPLC (High Performance Liquid Chromatography) on reversed-phase columns (C 18), using the methods below:
*The determination by LC-MS in the acidic range was carried out at pH 2.7 using 0.1% aqueous formic acid and acetonitrile (containing 0.1% formic acid) as mobile phases; linear gradient from 10% acetonitrile to 95% acetonitrile.
**The determination by LC-MS in the neutral range was carried out at pH 7.8 using 0.001 molar aqueous ammonium bicarbonate solution and acetonitrile as mobile phases; linear gradient from 10% acetonitrile to 95% acetonitrile.
Calibration was carried out using unbranched alkan-2-ones (having 3 to 16 carbon atoms) with known logP values (determination of the logP values by the retention times using linear interpolation between two successive alkanones).
The lambda-maX values were determined in the maxima of the chromatographic signals using the UV spectra from 200 nm to 400 nm.

B. BIOLOGICAL EXAMPLES

B.1 *Boophilus microplus* Test (BOOPMI Infection)

Solvent: Dimethyl Sulphoxide

To produce a suitable preparation of active compound, 10 mg of active compound are mixed with 0.5 ml of solvent, and the concentrate is diluted with water to the desired concentration. The active compound solution is injected into the abdomen (*Boophilus microplus*) and the animals are transferred into dishes and stored in a climatized room. The activity is monitored for deposition of fertile eggs. After 7 days, the activity in % is determined. 100% means that none of the ticks has laid fertile eggs.

In this test, for example, the following compounds of the Preparation Examples show an activity of 80% at an application rate of 20 μg/animal: 1-14

In this test, for example, the following compounds of the Preparation Examples show an activity of 95% at an application rate of 20 μg/animal: 1-2

In this test, for example, the following compounds of the Preparation Examples show an activity of 100% at an application rate of 20 μg/animal: 1-3, 1-5, 1-9, 1-11, 1-12, 1-13, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-38, 1-39, 1-40, 1-41, 1-42, 2-5, 2-6, 2-7, 2-8, 2-9, 2-11, 2-13, 2-14, 2-15, 2-16, 2-17, 2-18, 2-19, 2-20

B.2 *Ctenocephalides felis* Oral (CTECFE)

Solvent: 1 part by weight of dimethyl sulphoxide

To produce a suitable preparation of active compound, 10 mg of active compound are mixed with 0.5 ml of dimethyl sulphoxide. One part of the concentrate is diluted with citrated cattle blood, and the desired concentration is prepared.

20 unfed adult fleas (*Ctenocephalides felis*) are placed into a chamber whose top and bottom ends are closed with gauze. A metal cylinder whose bottom end is closed with parafilm is placed onto the chamber. The cylinder contains the blood/active compound preparation, which can be taken up by the fleas through the parafilm membrane. After 2 days, the kill in % is determined. 100% means that all fleas have been killed; 0% means that none of the fleas have been killed.

In this test, for example, the following compounds of the preparation examples show an activity of 80% at an application rate of 100 ppm: 1-34, 1-39, 2-1

In this test, for example, the following compounds of the preparation examples show an activity of 90% at an application rate of 100 ppm: 1-14, 1-31, 2-7, 2-9, 2-11, 2-15, 2-19

In this test, for example, the following compounds of the preparation examples show an activity of 95% at an application rate of 100 ppm: 1-13, 1-20, 1-28, 1-29, 1-42, 2-8

In this test, for example, the following compounds of the preparation examples show an activity of 100% at an application rate of 100 ppm: 1-2, 1-3, 1-9, 1-12, 1-15, 1-17, 1-18, 1-19, 1-21, 1-22, 1-23, 1-24, 1-25, 1-26, 1-27, 1-30, 1-32, 1-33, 1-35, 1-36, 1-38, 1-40, 1-41, 2-5, 2-6, 2-13, 2-14, 2-18

B.3 *Lucilia cuprina* Test (LUCICU)

Solvent: Dimethyl Sulphoxide

To produce a suitable preparation of active compound, 10 mg of active compound are mixed with 0.5 ml of dimethyl sulphoxide, and the concentrate is diluted with water to the desired concentration. Containers containing horse meat treated with the active compound preparation of the desired concentration are populated with *Lucilia cuprina* larvae.

After 2 days, the kill in % is determined. 100% means that all larvae have been killed; 0% means that none of the larvae have been killed.

In this test, for example, the following compounds of the preparation examples show an activity of 100% at an application rate of 100 ppm: 1-2, 1-3, 1-9, 1-11, 1-12, 1-13, 1-14, 1-15, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-38, 1-39, 1-40, 1-41, 1-42, 2-5, 2-6, 2-7, 2-8, 2-9, 2-11, 2-13, 2-14, 2-15, 2-16, 2-17, 2-18, 2-19, 2-20

B.4 Phaedon Test (PHAECO Spray Treatment)

Solvents: 78.0 parts by weight of acetone
1.5 parts by weight of dimethyl formamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration. Discs of Chinese cabbage leaves (*Brassica pekinensis*) are sprayed with an active compound preparation of the desired concentration and, after drying, populated with larvae of the mustard beetle (*Phaedon cochleariae*).

After 7 days, the activity in % is determined. 100% means that all beetle larvae have been killed; 0% means that none of the beetle larvae have been killed.

In this test, for example, the following compounds of the preparation examples show an activity of 100% at an application rate of 100 g/ha: Example Nos. 1-1, 1-2, 1-3, 1-4, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-38, 1-39, 1-40, 1-41, 1-42, 1-43, 1-44, 2-9, 2-12, 2-18, and 2-19.

B.5 *Spodoptera frugiperda* Test (SPODFR Spray Treatment)

Solvents: 78.0 parts by weight of acetone
1.5 parts by weight of dimethyl formamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration. Discs of maize leaves (*Zea mays*) are sprayed with an active compound preparation of the desired concentration and, after drying, populated with caterpillars of the army worm (*Spodoptera frugiperda*).

After 7 days, the activity in % is determined. 100% means that all caterpillars have been killed; 0% means that none of the caterpillars have been killed.

In this test, for example, the following compounds of the preparation examples show an activity of 83% at an application rate of 100 g/ha: Example No. 1-28.

In this test, for example, the following compounds of the preparation examples show an activity of 100% at an application rate of 100 g/ha: Example Nos. 1-9, 1-10, 1-11, 1-12, 1-13, 1-15, 1-17, 1-18, 1-19, 1-20, 1-21, 1-22, 1-23, 1-24, 1-25, 1-26, 1-29, 1-30, 1-33, 1-34, 1-35, 1-38, 1-40, 1-41, 1-42, 1-43, 1-44, 2-12, 2-18, and 2-19.

B.6 Myzus Test (MYZUPE Spray Treatment)

Solvents: 78 parts by weight of acetone
1.5 parts by weight of dimethyl formamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Discs of Chinese cabbage leaves (*Brassica pekinensis*) infested by all stages of the green peach affid (*Myzus persicae*) are sprayed with an active compound preparation of the desired concentration.

After 6 days, the activity in % is determined. 100% means that all affids have been killed; 0% means that none of the affids have been killed.

In this test, for example, the following compounds of the Preparation Examples show an activity of 80% at an application rate of 100 g/ha: Example No. 1-15.

In this test, for example, the following compounds of the Preparation Examples show an activity of 90% at an application rate of 100 g/ha: Example Nos. 1-11 and 1-34.

In this test, for example, the following compounds of the Preparation Examples show an activity of 100% at an application rate of 100 g/ha: Example Nos. 1-43 and 2-18.

B.7 *Tetranychus* Test, OP Resistant (TETRUR Spray Treatment)

Solvents: 78.0 parts by weight of acetone
1.5 parts by weight of dimethyl formamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration. Discs of bean leaves (*Phaseolus vulgaris*) which are infested by all stages of the greenhouse red spider mite (*Tetranychus urticae*) are sprayed with an active compound preparation of the desired concentration.

After 6 days, the activity in % is determined. 100% means that all spider mites have been killed; 0% means that none of the spider mites has been killed.

In this test, for example, the following compounds of the Preparation Examples show an activity of 90% at an application rate of 100 g/ha: Example Nos. 1-18, 1-21, 1-22, 1-35.

In this test, for example, the following components of the Preparation Examples show an activity of 100% at an application rate of 100 g/ha: Example Nos. 1-10, 1-12, 1-15, 1-17, 1-34, 1-38, 1-40, 1-41, 1-43, 1-44, 2-18, 2-19, 2-20.

B.8 Comparative Test

The advantageous biological activity of the compounds according to the invention can also be demonstrated in comparison to known compounds. Thus, the compounds (XX) to (XXIII) below, which are embraced by the general formula (I) described in WO 2008/077483, are synthesized as described therein and tested.

Compound (XX)

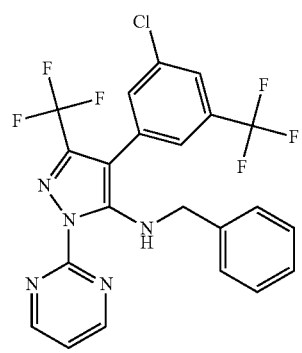

Compound (XXI)

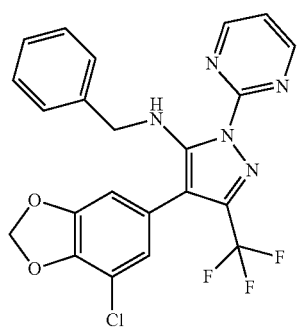

Compound (XXII)

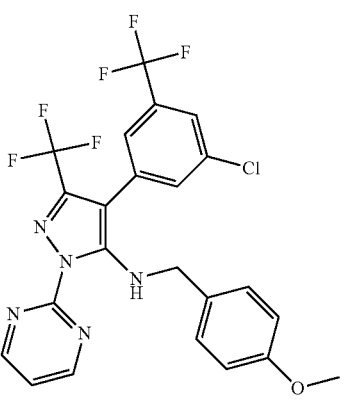

Compound (XXIII)

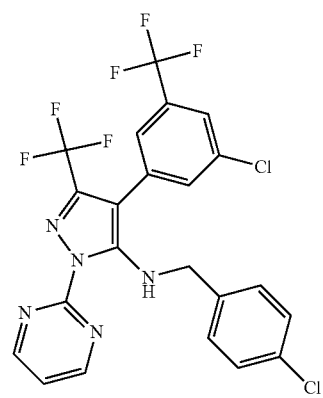

Comparative Test B.8-1: Phaedon Test (PHAECO Spray Treatment)

The test was carried out and evaluated as described in Example B.4.

In this test, the compound (XX) showed, at a concentration of 4 g/ha, no (i.e. 0%) activity, whereas compound No. 1-12 has an activity of 100% at the same concentration.

At a concentration of 100 g/ha, the compound (XXII) showed no activity, whereas the compound No. 1-17 has an activity of 100% at the same concentration.

At a concentration of 20 g/ha, the compound (XXIII) showed no activity, whereas the compound No. 1-16 has an activity of 100% at the same concentration.

Comparative Test B.8-2: *Spodoptera frueiperda* Test (SPODFR Spray Treatment)

The test was carried out and evaluated as described in Example B.5.

In this test, the compounds (XX) and (XXI) showed, at a concentration of 20 g/ha, no (i.e. 0%) activity, whereas the compound No. 1-12 has an activity of 100% and the compound No. 1-18 has an activity of 67% at the same concentration.

At a concentration of 100 g/ha, the compound (XXII) showed no activity, whereas the compound No. 1-17 has an activity of 100% at the same concentration.

Comparative Test B.8-3: *Tetranychus* Test; OP Resistant (TETRUR Spray Treatment)

The test was carried out and evaluated as described in Example B.7.

In this test, the compound (XXI) showed, at a concentration of 20 g/ha, no (i.e. 0%) activity, whereas the compound No. 1-18 had an activity of at least 90% at the same concentration.

At a concentration of 100 g/ha, the compound (XXII) showed no activity, whereas the compound No. 1-17 has an activity of 100% at the same concentration.

Test B.9 *Musca domestica* Test (MUSCDO)

Solvent: Dimethyl sulphoxide

To prepare a suitable preparation of active compound, 10 mg of active component are mixed with 0.5 ml of dimethyl sulphoxide, and the concentrate is diluted with water to the desired concentration. Vessels containing a sponge which had been treated with the active compound preparation of the desired concentration are populated with adult *Musca domestica*.

After the desired period of time, the kill in % is determined. 100% means that all flies have been killed; 0% means that none of the flies have been killed.

In this test, for example, the following compounds of the Preparation Examples show an activity of 80% at an application rate of 20 ppm: 1-18

In this test, for example, the following compounds of the Preparation Examples show an activity of 80% at an application rate of 100 ppm: 1-11, 1-14, 1-15, 1-24, 1-27, 2-13, 2-20

In this test, for example, the following compounds of the Preparation Examples show an activity of 90% at an application rate of 20 ppm: 1-31

In this test, for example, the following compounds of the Preparation Examples show an activity of 90% at an application rate of 100 ppm: 2-7, 2-11, 2-14, 2-16

In this test, for example, the following compounds of the Preparation Examples show an activity of 100% at an application rate of 20 ppm: 1-12, 1-13, 1-17, 1-25, 1-35, 1-36, 1-38, 2-9, 2-19

In this test, for example, the following compounds of the Preparation. Examples show an activity of 100% at an application rate of 100 ppm: 1-19, 1-20, 1-21, 1-28, 1-29, 1-34, 1-39, 1-40, 1-41, 1-42, 2-17

Test B.10 Boophilus microplus Test (DIP)

Test animals: adult fed females of the Boophilus microplus strain Parkhurst (SP-resistant)
Solvent: Dimethyl sulphoxide 10 mg of active compound are dissolved in 0.5 ml of dimethyl sulphoxide. To produce a suitable formulation, the active compound solution is diluted with water to the particular desired concentration. This active compound preparation is pipetted into tubes. 8-10 ticks are transferred into a further tube provided with holes. The tube is dipped into the active compound preparation, with all ticks being wetted completely. After the liquid has run off, the ticks are transferred to filter discs in plastic dishes and kept in a climatized room. After the desired period of time, the activity is checked for deposition of fertile eggs. Eggs whose fertility is not visible from the outside are kept in glass tubes in a climatized cupboard under the larvae have hatched. An activity of 100% means that no tick has laid fertile eggs.

In this test, for example, the following compounds of the Preparation Examples show an activity of 80% at an application rate of 100 ppm: 2-19

In this test, for example, the following compounds of the Preparation Examples show an activity of 90% at an application rate of 100 ppm: 2-11

In this test, for example, the following compounds of the Preparation Examples show an activity of 100% at an application rate of 100 ppm: 1-18, 1-22, 1-23, 1-24, 1-25, 1-26, 1-27, 1-30, 1-33, 1-35, 1-36, 1-38, 2-6, 2-7, 2-8, 2-13, 2-14, 2-16, 2-17, 2-18

The invention claimed is:
1. A compound of the formula (I)

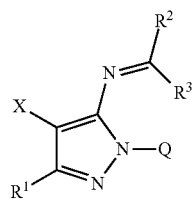

(I)

or a salt or N-oxide thereof, in which
X represents substituted aryl or heteroaryl;
$R^1$ represents $C_1$-$C_6$-alkyl which is optionally substituted by one or more substituents selected from the group consisting of $C_1$-$C_6$-alkoxy, halo-$C_1$-$C_6$-alkoxy, $C_1$-$C_6$-alkylsulphanyl, halo-$C_1$-$C_6$-alkylsulphanyl, $C_1$-$C_6$-alkylsulphinyl, halo-$C_1$-$C_6$-alkylsulphinyl, $C_1$-$C_6$-alkylsulphonyl, halo-$C_1$-$C_6$-alkylsulphonyl, $C_1$-$C_6$-alkylcarbonyl, $C_1$-$C_6$-alkoxycarbonyl, hydroxyl, and $C_3$-$C_6$-cycloalkyl; $C_2$-$C_6$-alkenyl which is optionally substituted by one or more substituents selected from the group consisting of halogen, $C_1$-$C_6$-alkoxy, halo-$C_1$-$C_6$-alkoxy, $C_1$-$C_6$-alkylsulphanyl, halo-$C_1$-$C_6$-alkylsulphanyl, $C_1$-$C_6$-alkylsulphinyl, halo-$C_1$-$C_6$-alkylsulphinyl, $C_1$-$C_6$-alkylsulphonyl, halo-$C_1$-$C_6$-alkylsulphonyl, $C_1$-$C_6$-alkylcarbonyl, $C_1$-$C_6$-alkoxycarbonyl, and $C_3$-$C_6$-cycloalkyl; $C_3$-$C_6$-cycloalkyl which is optionally substituted by one or more substituents selected from the group consisting of $C_1$-$C_6$-alkyl, halo-$C_1$-$C_6$-alkyl, and halogen; halo-$C_1$-$C_6$-alkyl which is optionally substituted by one or more substituents selected from the group consisting of $C_1$-$C_6$-alkoxy, $C_1$-$C_6$-alkylsulphanyl, halo-$C_1$-$C_6$-alkylsulphanyl, $C_1$-$C_6$-alkylsulphinyl, halo-$C_1$-$C_6$-alkylsulphinyl, $C_1$-$C_6$-alkylsulphonyl, halo-$C_1$-$C_6$-alkylsulphonyl, and phenyl, wherein the phenyl is optionally substituted by one or more substituents independently selected from the group consisting of halogen, $C_1$-$C_6$-alkyl, halo-$C_1$-$C_6$-alkyl, and $C_1$-$C_6$-alkoxy; phenyl which is optionally substituted by one or more substituents selected from the group consisting of halogen, $C_1$-$C_6$-alkyl, halo-$C_1$-$C_6$-alkyl, and $C_1$-$C_6$-alkoxy; benzyl which is optionally substituted by one or more substituents selected from the group consisting of halogen, $C_1$-$C_6$-alkyl, halo-$C_1$-$C_6$-alkyl, and $C_1$-$C_6$-alkoxy; cyano; formyl; $C_1$-$C_6$-alkylcarbonyl; —CH=NO—H; —CH=NO—$C_1$-$C_6$-alkyl; —CH=NO-halo-$C_1$-$C_6$-alkyl; —C(CH$_3$)=NO—H; —C(CH$_3$)=NO—$C_1$-$C_6$-alkyl; or —C(CH$_3$)=NO-halo-$C_1$-$C_6$-alkyl;
$R^2$ represents hydrogen; $C_1$-$C_6$-alkyl which is optionally substituted by one or more subsituents selected from the group consisting of $C_1$-$C_6$-alkoxy, halo-$C_1$-$C_6$-alkoxy, $C_1$-$C_6$-alkylsulphanyl, halo-$C_1$-$C_6$-alkylsulphanyl, $C_1$-$C_6$-alkylsulphinyl, halo-$C_1$-$C_6$-alkylsulphinyl, $C_1$-$C_6$-alkylsulphonyl, halo-$C_1$-$C_6$-alkylsulphonyl, $C_1$-$C_6$-alkylcarbonyl, $C_1$-$C_6$-alkoxycarbonyl, hydroxyl, and $C_3$-$C_6$-cycloalkyl; $C_2$-$C_6$-alkenyl which is optionally substituted by one or more substituents selected from the group consisting of halogen, $C_1$-$C_6$-alkoxy, halo-$C_1$-$C_6$-alkoxy, $C_1$-$C_6$-alkylsulphanyl, halo-$C_1$-$C_6$-alkylsulphanyl, $C_1$-$C_6$-alkylsulphinyl, halo-$C_1$-$C_6$-alkylsulphinyl, $C_1$-$C_6$-alkylsulphonyl, halo-$C_1$-$C_6$-alkylsulphonyl, $C_1$-$C_6$-alkylcarbonyl, $C_1$-$C_6$-alkoxycarbonyl, and $C_3$-$C_6$-cycloalkyl; $C_3$-$C_6$-cycloalkyl which is optionally substituted by one or more substituents selected from the group consisting of $C_1$-$C_6$-alkyl, halo-$C_1$-$C_6$-alkyl, and halogen; halo-$C_1$-$C_6$-alkyl which is optionally substituted by one or more substituents selected from the group consisting of $C_1$-$C_6$-alkoxy, $C_1$-$C_6$-alkylsulphanyl, halo-$C_1$-$C_6$-alkylsulphanyl, $C_1$-$C_6$-alkylsulphinyl, halo-$C_1$-$C_6$-alkylsulphinyl, $C_1$-$C_6$-alkylsulphonyl, halo-$C_1$-$C_6$-alkylsulphonyl, and phenyl, wherein the phenyl is optionally substituted by one or more substituents independently selected from the group consisting of halogen, $C_1$-$C_6$-alkyl, halo-$C_1$-$C_6$-alkyl, and $C_1$-$C_6$-alkoxy; phenyl which is optionally substituted by one or more substituents selected from the group consisting of halogen, $C_1$-$C_6$-alkyl, halo-$C_1$-$C_6$-alkyl, hydroxyl, and $C_1$-$C_6$-alkoxy; heteroaryl which is optionally substituted by one or more substituents selected from the group consisting of —OH, —SH, —NH$_2$, halogen, $C_1$-$C_6$-alkyl, halo-$C_1$-$C_6$-alkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro, and cyano; heterocyclyl which is optionally substituted by one or more substituents selected from the group consisting of —OH, =O, —SH, =S, —NH$_2$, halogen, $C_1$-$C_6$-alkyl, halo-$C_1$-$C_6$-alkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro, and cyano; benzyl which is optionally substituted by one or more substituents selected from the group consisting of halogen, $C_1$-$C_6$-alkyl, halo-$C_1$-$C_6$-alkyl, and $C_1$-$C_6$-alkoxy; heteroaryl-$C_1$-$C_3$-alkyl which is optionally substituted by one or more of the substituents selected from the group consisting of —OH, —SH, —NH$_2$, halogen, $C_1$-$C_6$-alkyl, halo-$C_1$-$C_6$-alkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro, and cyano; heteroaryl-$C_1$-$C_3$-alkyl which is optionally substituted by one or more substituents selected from the group consisting of —OH, =O, —SH, =S, —$NH_2$, halogen, $C_1$-$C_6$-alkyl, halo-$C_1$-$C_6$-alkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro, and cyano; chlorine; cyano; formyl; $C_1$-$C_6$-alkylcarbonyl; —CH=NO—H; —CH=NO—$C_1$-$C_6$-alkyl; —CH=NO-halo-$C_1$-$C_6$-alkyl; —C($CH_3$)=NO—H; —C($CH_3$)=NO—$C_1$-$C_6$-alkyl; or —C($CH_3$)=NO-halo-$C_1$-$C_6$-alkyl;

$R^3$ represents $C_1$-$C_6$-alkyl which is optionally substituted by one or more substituents selected from the group consisting of $C_1$-$C_6$-alkoxy, halo-$C_1$-$C_6$-alkoxy, $C_1$-$C_6$-alkylsulphanyl, halo-$C_1$-$C_6$-alkylsulphanyl, $C_1$-$C_6$-alkylsulphinyl, halo-$C_1$-$C_6$-alkylsulphinyl, $C_1$-$C_6$-alkylsulphonyl, halo-$C_1$-$C_6$-alkylsulphonyl, $C_1$-$C_6$-alkylcarbonyl, $C_1$-$C_6$-alkoxycarbonyl, hydroxyl, and $C_3$-$C_6$-cycloalkyl; $C_2$-$C_6$-alkenyl which is optionally substituted by one or more substituents selected from the group consisting of halogen, $C_1$-$C_6$-alkoxy, halo-$C_1$-$C_6$-alkoxy, $C_1$-$C_6$-alkylsulphanyl, halo-$C_1$-$C_6$-alkylsulphanyl, $C_1$-$C_6$-alkylsulphinyl, halo-$C_1$-$C_6$-alkylsulphinyl, $C_1$-$C_6$-alkylsulphonyl, halo-$C_1$-$C_6$-alkylsulphonyl, $C_1$-$C_6$-alkylcarbonyl, $C_1$-$C_6$-alkoxycarbonyl, and $C_3$-$C_6$-cycloalkyl; $C_3$-$C_6$-cycloalkyl which is optionally substituted by one or more substituents selected from the group consisting of $C_1$-$C_6$-alkyl, halo-$C_1$-$C_6$-alkyl, and halogen; halo-$C_1$-$C_6$-alkyl which is optionally substituted by one or more substituents selected from the group consisting of $C_1$-$C_6$-alkoxy, $C_1$-$C_6$-alkylsulphanyl, halo-$C_1$-$C_6$-alkylsulphanyl, $C_1$-$C_6$-alkylsulphinyl, halo-$C_1$-$C_6$-alkylsulphinyl, $C_1$-$C_6$-alkylsulphonyl, halo-$C_1$-$C_6$-alkylsulphonyl, and phenyl, wherein the phenyl is optionally substituted by one or more substituents independently selected from the group consisting of halogen, $C_1$-$C_6$-alkyl, halo-$C_1$-$C_6$-alkyl, and $C_1$-$C_6$-alkoxy; phenyl which is optionally substituted by one or more substituents selected from the group consisting of halogen, $C_1$-$C_6$-alkyl, halo-$C_1$-$C_6$-alkyl, hydroxyl, and $C_1$-$C_6$-alkoxy; heteroaryl which is optionally substituted by one or more substituents selected from the group consisting of —OH, —SH, —$NH_2$, halogen, $C_1$-$C_6$-alkyl, halo-$C_1$-$C_6$-alkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro, and cyano; heterocyclyl which is optionally substituted by one or more substituents selected from the group consisting of —OH, =O, —SH, =S, —$NH_2$, halogen, $C_1$-$C_6$-alkyl, halo-$C_1$-$C_6$-alkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro, and cyano; benzyl which is optionally substituted by one or more substituents selected from the group consisting of halogen, $C_1$-$C_6$-alkyl, halo-$C_1$-$C_6$-alkyl, and $C_1$-$C_6$-alkoxy; heteroaryl-$C_1$-$C_3$-alkyl which is optionally substituted by one or more substituents selected from the group consisting of —OH, —SH, —$NH_2$, halogen, $C_1$-$C_6$-alkyl, halo-$C_1$-$C_6$-alkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro, and cyano; heterocyclyl-$C_1$-$C_3$-alkyl which is optionally substituted by one or more substituents selected from the group consisting of OH, =O, —SH, =S, —$NH_2$, halogen, $C_1$-$C_6$-alkyl, halo-$C_1$-$C_6$-alkyl, $C_1$-$C_6$-alkoxy, $C_1$-$C_6$-alkylsulphanyl, $C_1$-$C_6$-alkylsulphinyl, $C_1$-$C_6$-alkylsulphonyl, mono-$C_1$-$C_6$-alkylamino, di-$C_1$-$C_6$-alkylamino, nitro, and cyano; chlorine; cyano; formyl; $C_1$-$C_6$-alkylcarbonyl; —CH—NO—H; —CH=NO—$C_1$-$C_6$-alkyl; —CH=NO-halo-$C_1$-$C_6$-alkyl; —C($CH_3$)=NO—H; —C($CH_3$)=NO—$C_1$-$C_6$-alkyl; —C($CH_3$)=NO-halo-$C_1$-$C_6$-alkyl; $C_1$-$C_6$-alkoxy; $C_3$-$C_6$-cycloalkoxy; $C_3$-$C_6$-cycloalkyl-$C_1$-$C_6$-alkoxy; halo-$C_1$-$C_6$-alkoxy; $C_2$-$C_6$-alkenyloxy; $C_2$-$C_6$-alkynyloxy; benzyloxy which is optionally substituted by one or more substituents selected from the group consisting of halogen, $C_1$-$C_6$-alkyl, halo-$C_1$-$C_6$-alkyl, and $C_1$-$C_6$-alkoxy; $C_1$-$C_6$-alkylsulphanyl; $C_1$-$C_6$-alkylsulphinyl; $C_1$-$C_6$-alkylsulphonyl; phenylsulphanyl, phenylsulphinyl, or phenylsulphonyl, each of which is optionally substituted at the phenyl group by one or more substituents selected from the group consisting of halogen, $C_1$-$C_6$-alkyl, halo-$C_1$-$C_6$-alkyl, and $C_1$-$C_6$-alkoxy; amino which is mono- or disubstituted by one or more substituents selected from the group consisting of $C_1$-$C_6$-alkyl, halo-$C_1$-$C_6$-alkyl, $C_2$-$C_6$-alkenyl, $C_2$-$C_6$-alkynyl, benzyl which is optionally substituted by one or more substituents selected from the group consisting of halogen, $C_1$-$C_6$-alkyl, $C_1$-$C_6$-haloalkyl, $C_1$-$C_6$-alkoxy, and phenyl which is optionally substituted by one or more substituents selected from the group consisting of OH, halogen, $C_1$-$C_6$-alkyl, halo-$C_1$-$C_6$-alkyl, and $C_1$-$C_6$-alkoxy; or amino as a component of a five- or six-membered heterocyclic ring which is attached via the amino nitrogen and, as additional heteroatom, may contain oxygen and/or nitrogen;

Q represents a chemical grouping $Q^2$

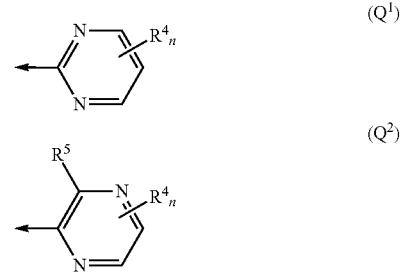

in which $R^4$ represents halogen, $C_1$-$C_6$-alkyl, $C_3$-$C_6$-cycloalkyl, halo-$C_1$-$C_6$-alkyl, cyano, formyl, $C_1$-$C_6$-alkylcarbonyl, —CH=NO—H, —CH=NO—$C_1$-$C_6$-alkyl, —CH=NO-halo-$C_1$-$C_6$-alkyl, —C($CH_3$)=NO—H, —C($CH_3$)=NO—$C_1$-$C_6$-alkyl, —C($CH_3$)=NO-halo-$C_1$-$C_6$-alkyl, nitro, amino, hydroxyl, SH, $C_1$-$C_6$-alkoxy, $C_1$-$C_6$-alkylsulphanyl, halo-$C_1$-$C_6$-alkylsulphanyl, $C_1$-$C_6$-alkylsulphinyl, halo-$C_1$-$C_6$-alkylsulphinyl, $C_1$-$C_6$-alkylsulphonyl, or halo-$C_1$-$C_6$-alkylsulphonyl;

n represents 0, 1, 2, or 3;

$R^5$ represents hydrogen, halogen, $C_1$-$C_6$-alkyl, halo-$C_1$-$C_6$-alkyl, hydroxyl, $C_1$-$C_6$-alkoxy, $C_1$-$C_6$-alkoxy-$C_1$-$C_6$-alkyl, $C_1$-$C_6$-alkoxy-$C_1$-$C_6$-alkoxy, $C_3$-$C_6$-cycloalkyl, $C_2$-$C_6$-alkenyloxy, $C_2$-$C_6$-alkynyloxy, benzyloxy, $C_3$-$C_6$-cycloalkyl-$C_1$-$C_6$-alkoxy, halo-$C_1$-$C_6$-alkoxy, halo-$C_1$-$C_6$-alkoxy-$C_1$-$C_6$-alkyl, —SH, $C_1$-$C_6$-alkylsulphanyl, halo-$C_1$-$C_6$-alkylsulphanyl, $C_1$-$C_6$-alkylsulphinyl, halo-$C_1$-$C_6$-alkylsulphinyl, $C_1$-$C_6$-alkylsulphonyl, halo-$C_1$-$C_6$-alkylsulphonyl, cyano, nitro, $C_1$-$C_6$-alkylcarbonyl, $C_1$-$C_6$-alkoxycarbonyl, $C_1$-$C_6$-alkoxycarbonyl-$C_1$-$C_6$-alkyl, carboxyl, carboxamide, di-$C_1$-$C_6$-alkylcarboxamide, tri-$C_1$-$C_6$-alkylsilyl, nitro, amino, $C_1$-$C_6$-alkylamino, di-$C_1$-$C_6$-alkylamino, $C_1$-$C_6$-alkylsulphonylamino, di-$C_1$-$C_6$-alkylsulphonylamino, formyl, —CH=NO—H, —CH=NO—$C_1$-$C_6$-alkyl, —CH=NO-halo-$C_1$-$C_6$-alkyl, —C(CH$_3$)=NO—H, —C(CH$_3$)=NO—$C_1$-$C_6$-alkyl, —C(CH$_3$)=NO-halo-$C_1$-$C_6$-alkyl, or heteroaryl which is optionally substituted by one or more substituents selected from the group consisting of halogen, $C_1$-$C_6$-alkyl, halo-$C_1$-$C_6$-alkyl, and $C_1$-$C_6$-alkoxy.

2. The compound of claim 1, wherein X is phenyl, 2-pyridyl, or 3-pyridyl, any of which is substituted by one or more Y, where Y represents halogen, cyano, nitro, $C_1$-$C_6$-alkyl, halo-$C_1$-$C_6$-alkyl, $C_1$-$C_6$-alkoxy, $C_1$-$C_6$-alkoxy-$C_1$-$C_6$-alkyl, $C_1$-$C_6$-alkoxy-$C_1$-$C_6$-alkoxy, $C_3$-$C_6$-cycloalkyl, $C_2$-$C_6$-alkenyloxy, $C_2$-$C_6$-alkynyloxy, benzyloxy, $C_3$-$C_6$-cycloalkyl-$C_1$-$C_6$-alkoxy, halo-$C_1$-$C_6$-alkoxy, halo-$C_1$-$C_6$-alkoxy-$C_1$-$C_6$-alkyl, $C_1$-$C_6$-alkylsulphanyl, halo-$C_1$-$C_6$-alkylsulphanyl, $C_1$-$C_6$-alkylsulphinyl, halo-$C_1$-$C_6$-alkylsulphinyl, $C_1$-$C_6$-alkylsulphonyl, halo-$C_1$-$C_6$-alkylsulphonyl, $C_1$-$C_6$-alkylcarbonyl, $C_1$-$C_6$-alkoxycarbonyl, $C_1$-$C_6$-alkoxycarbonyl-$C_1$-$C_6$-alkyl, carboxyl, carboxamide, di-$C_1$-$C_6$-alkylcarboxamide, tri-$C_1$-$C_6$-alkylsilyl, amino, $C_1$-$C_6$-alkylamino, di-$C_1$-$C_6$-alkylamino, $C_1$-$C_6$-alkylsulphonylamino, di-$C_1$-$C_6$-alkylsulphonylamino, formyl, —CH=NO—H, —CH=NO—$C_1$-$C_6$-alkyl, —CH=NO-halo-$C_1$-$C_6$-alkyl, —C(CH$_3$)=NO—H, —C(CH$_3$)=NO—$C_1$-$C_6$-alkyl, —C(CH$_3$)=NO-halo-$C_1$-$C_6$-alkyl, or where, if two substituents represent two vicinal $C_1$-$C_6$-alkyl-, halo-$C_1$-$C_6$-alkyl-, $C_1$-$C_6$-alkoxy-, or halo-$C_1$-$C_6$-alkoxy groups, the substituents together with the carbon atoms to which they are attached form a five- or six-membered cyclic system which contains 0 to 2 oxygen or nitrogen atoms, where the carbon atoms of the cyclic system are optionally substituted by one or more substituents independently selected from the group consisting of halogen and $C_1$-$C_6$-alkyl.

3. A composition comprising one or more compounds of formula (I) according to claim 1 for controlling unwanted plant pests.

4. A method for controlling unwanted plant pests, comprising applying an effective amount of one or more compounds of formula (I) according to claim 1 to a plant, a plant part, or surroundings of a plant.

5. A method for protecting transgenic or conventional seed and the plant originating therefrom against attack by pests, comprising treating the seed with an effective amount of one or more compounds of formula (I) according to claim 1.

6. A method for controlling plant pests, comprising applying an effective amount of one or more compounds of formula (I) according to claim 1 to a plant pest, surroundings of a plant pest, or habitat of a plant pest.

* * * * *